US012396630B2

(12) United States Patent
Kaji et al.

(10) Patent No.: US 12,396,630 B2
(45) Date of Patent: Aug. 26, 2025

(54) IMAGING SUPPORT DEVICE, SCANNER SYSTEM, AND IMAGING SUPPORT METHOD

(71) Applicant: J. MORITA MFG. CORP., Kyoto (JP)

(72) Inventors: Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 579 days.

(21) Appl. No.: 17/421,235

(22) PCT Filed: Jan. 6, 2020

(86) PCT No.: PCT/JP2020/000034
§ 371 (c)(1),
(2) Date: Jul. 7, 2021

(87) PCT Pub. No.: WO2020/145225
PCT Pub. Date: Jul. 16, 2020

(65) Prior Publication Data
US 2022/0117480 A1 Apr. 21, 2022

(30) Foreign Application Priority Data
Jan. 8, 2019 (JP) .................................. 2019-001021

(51) Int. Cl.
A61B 1/24 (2006.01)
A61B 1/00 (2006.01)
(Continued)

(52) U.S. Cl.
CPC .......... A61B 1/24 (2013.01); A61B 1/000094 (2022.02); A61B 1/04 (2013.01);
(Continued)

(58) Field of Classification Search
CPC ....... A61B 1/24; A61B 1/000094; A61B 1/04; A61C 9/0053
See application file for complete search history.

(56) References Cited

U.S. PATENT DOCUMENTS

2015/0320320 A1* 11/2015 Kopelman .............. G06T 7/579
433/215
2017/0340419 A1* 11/2017 Ohtake .............. A61C 13/0004
(Continued)

FOREIGN PATENT DOCUMENTS

EP 3 901 901 A1 10/2021
JP 2009517144 A 4/2009
(Continued)

OTHER PUBLICATIONS

Office Action issued in counterpart Japanese Patent Application No. 2019-001021 mailed on Jan. 10, 2023 (5 pages).
(Continued)

Primary Examiner — David Bilodeau
(74) Attorney, Agent, or Firm — Osha Bergman Watanabe & Burton LLP

(57) ABSTRACT

An imaging support device that supports imaging of teeth inside an oral cavity is provided. The imaging support device includes an input unit, an identification unit, a specification unit, and an output unit. The input unit receives a tooth image obtained by imaging the teeth inside the oral cavity. The identification unit identifies a type of a tooth based on the tooth image received by the input unit. Based on the type of the tooth identified by the identification unit, the specification unit specifies a type of a tooth as a target for imaging support. The output unit outputs information about the type of the tooth specified by the specification unit to an outside at a prescribed timing.

17 Claims, 13 Drawing Sheets

(51) Int. Cl.
*A61B 1/04* (2006.01)
*A61C 9/00* (2006.01)
*G06V 40/10* (2022.01)
*G06V 10/82* (2022.01)

(52) U.S. Cl.
CPC ............ *A61C 9/0053* (2013.01); *G06V 10/82* (2022.01); *G06V 40/10* (2022.01)

(56) References Cited

U.S. PATENT DOCUMENTS

| | | | |
|---|---|---|---|
| 2017/0367789 A1* | 12/2017 | Fujiwara | A61C 5/77 |
| 2018/0168781 A1* | 6/2018 | Kopelman | A61B 34/10 |
| 2018/0296131 A1* | 10/2018 | Kaji | G01B 11/24 |
| 2019/0175303 A1* | 6/2019 | Akopov | A61C 7/002 |
| 2020/0297187 A1* | 9/2020 | Wakazome | A61B 1/24 |

FOREIGN PATENT DOCUMENTS

| | | |
|---|---|---|
| JP | 2009523552 A | 6/2009 |
| JP | 2011-212234 A | 10/2011 |
| JP | 2012245064 A | 12/2012 |
| JP | 2017521113 A | 8/2017 |
| JP | 2017213060 A | 12/2017 |
| WO | 2007062658 A2 | 6/2007 |
| WO | 2007084647 A2 | 7/2007 |
| WO | 2015170162 A1 | 11/2015 |
| WO | 2016143022 A1 | 9/2016 |
| WO | 2017111116 A1 | 6/2017 |
| WO | 2018/167530 A1 | 9/2018 |

OTHER PUBLICATIONS

International Search Report issued in International Application No. PCT/JP2020/000034, mailed Mar. 17, 2020 (5 pages).
Written Opinion issued in International Application No. PCT/JP2020/000034; Dated Mar. 17, 2020 (6 pages).
Extended European Search Report in counterpart European Application No. 20 73 8722.6 issued Aug. 19, 2022 (7 pages).
Office Action issued in Japanese Application No. 2019-001021; Dated Jan. 18, 2022 (13 pages).

* cited by examiner

FIG.8

| DATA ACQUISITION SITE | IMAGING DIRECTION | | |
|---|---|---|---|
| INCISOR IN UPPER JAW | PLANE ON UPPER LIP SIDE | PLANE ON PALATE SIDE | PLANE ON INCISAL EDGE SIDE |
| CANINE IN UPPER JAW | PLANE ON BUCCAL SIDE | PLANE ON PALATE SIDE | PLANE OF OCCLUSION |
| MOLAR IN UPPER JAW | PLANE ON BUCCAL SIDE | PLANE ON PALATE SIDE | PLANE OF OCCLUSION |
| INCISOR IN LOWER JAW | PLANE ON LOWER LIP SIDE | PLANE ON TONGUE SIDE | PLANE ON INCISAL EDGE SIDE |
| CANINE IN LOWER JAW | PLANE ON BUCCAL SIDE | PLANE ON TONGUE SIDE | PLANE OF OCCLUSION |
| MOLAR IN LOWER JAW | PLANE ON BUCCAL SIDE | PLANE ON TONGUE SIDE | PLANE OF OCCLUSION |

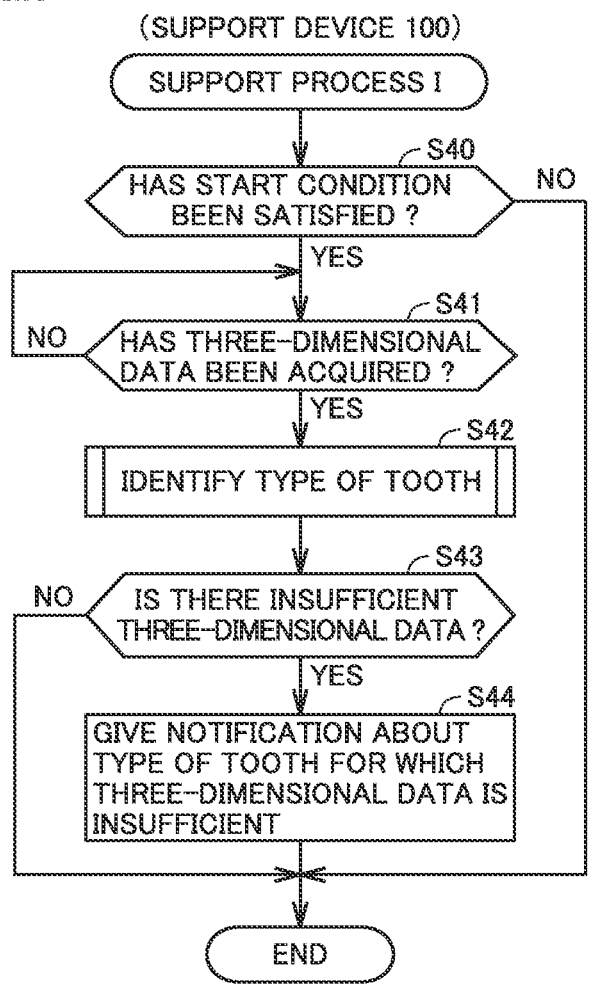

IMAGING SUPPORT DEVICE, SCANNER SYSTEM, AND IMAGING SUPPORT METHOD

TECHNICAL FIELD

The present invention relates to an imaging support device, a scanner system including the imaging support device, and an imaging support method.

BACKGROUND ART

In the dental field, various devices have been developed as imaging devices for imaging the inside of an oral cavity. For example, a scanner device for obtaining three-dimensional (3D) data of a dental site inside the oral cavity of a patient has been developed as an imaging device. However, when the scanner device is used to scan the inside of the oral cavity to acquire three-dimensional data of a dental arch, an overlapping area, a defect area, or the like occurs among a plurality of captured images depending on the user's operation.

Accordingly, in PTL 1, such an overlapping area and a defect area can be identified and displayed as an area of interest in the image captured by the scanner device. Thus, immediately after the user uses the scanner device to captures one or more images, the user can be notified of the area of interest that needs to be re-scanned, thereby allowing easy, quick and accurate scanning with the scanner device.

CITATION LIST

Patent Literature

PTL 1: Japanese National Patent Publication No. 2017-521113

SUMMARY OF INVENTION

Technical Problem

In PTL 1, when the user uses the scanner device to capture an image of a dental arch, the image of the dental arch includes gums and a plurality of teeth, and additionally a plurality of areas of interest. However, by merely showing the area of interest in the image of the dental arch, it cannot be sometimes easily recognized as to which tooth in the dental arch shows an area of interest.

Further, in PTL 1, it cannot be sometimes easily recognized as to which tooth inside the oral cavity of an actual patient corresponds to the tooth having the area of interest shown in the image of the dental arch. Thus, by merely showing an area of interest in the image of the dental arch, there is a limit on imaging support for the scanner device.

The present invention has been made in order to solve the above-described problems, and an object of the present invention is to provide an imaging support device capable of outputting information as a target for imaging support in an imaging device that images an inside of an oral cavity, a scanner system including the imaging support device, and an imaging support method.

Solution to Problem

An imaging support device according to the present invention is an imaging support device that supports imaging of teeth inside an oral cavity, and includes: an input unit that receives a tooth image obtained by imaging the teeth inside the oral cavity; an identification unit that identifies a type of a tooth based on the tooth image received by the input unit; a specification unit that, based on the type of the tooth identified by the identification unit, specifies a type of a tooth as a target for imaging support; and an output unit that outputs information about the type of the tooth specified by the specification unit to an outside at a prescribed timing.

A scanner system according to the present invention is a scanner system that acquires shape information of a tooth, and includes: a three-dimensional scanner that images teeth using a three-dimensional camera; and an imaging support device that identifies a type of a tooth based on a tooth image in three dimensions that is acquired by the three-dimensional scanner, and gives a notification about the identified type of the tooth. The imaging support device includes: an input unit that receives a tooth image obtained by imaging teeth inside an oral cavity; an identification unit that identifies a type of a tooth based on the tooth image received by the input unit; a specification unit that, based on the type of the tooth identified by the identification unit, specifies a type of a tooth as a target to be imaged; and an output unit that outputs information about the type of the tooth specified by the specification unit to an outside at a prescribed timing.

An imaging support method according to the present invention is an imaging support method of supporting imaging of teeth inside an oral cavity, and includes: receiving a tooth image obtained by imaging the teeth inside the oral cavity; identifying a type of a tooth based on the received tooth image; based on the identified type of the tooth, specifying a type of a tooth as a target to be imaged; and outputting information about the specified type of the tooth to an outside at a prescribed timing.

Advantageous Effects of Invention

The imaging support device according to the present invention specifies a type of a tooth as a target for imaging support based on the type of the tooth identified by the identification unit, and thereby can output the information for imaging support to a user so as to allow the user to easily recognize which tooth inside the oral cavity corresponds to the tooth as a target for imaging support.

BRIEF DESCRIPTION OF DRAWINGS

FIG. 8 is a schematic diagram showing examples of teeth to be identified in the identification process according to the present first embodiment.

FIG. 9 is a flowchart for illustrating an example of a support process performed by the imaging support device according to the present first embodiment.

DESCRIPTION OF EMBODIMENTS

Figure 1:
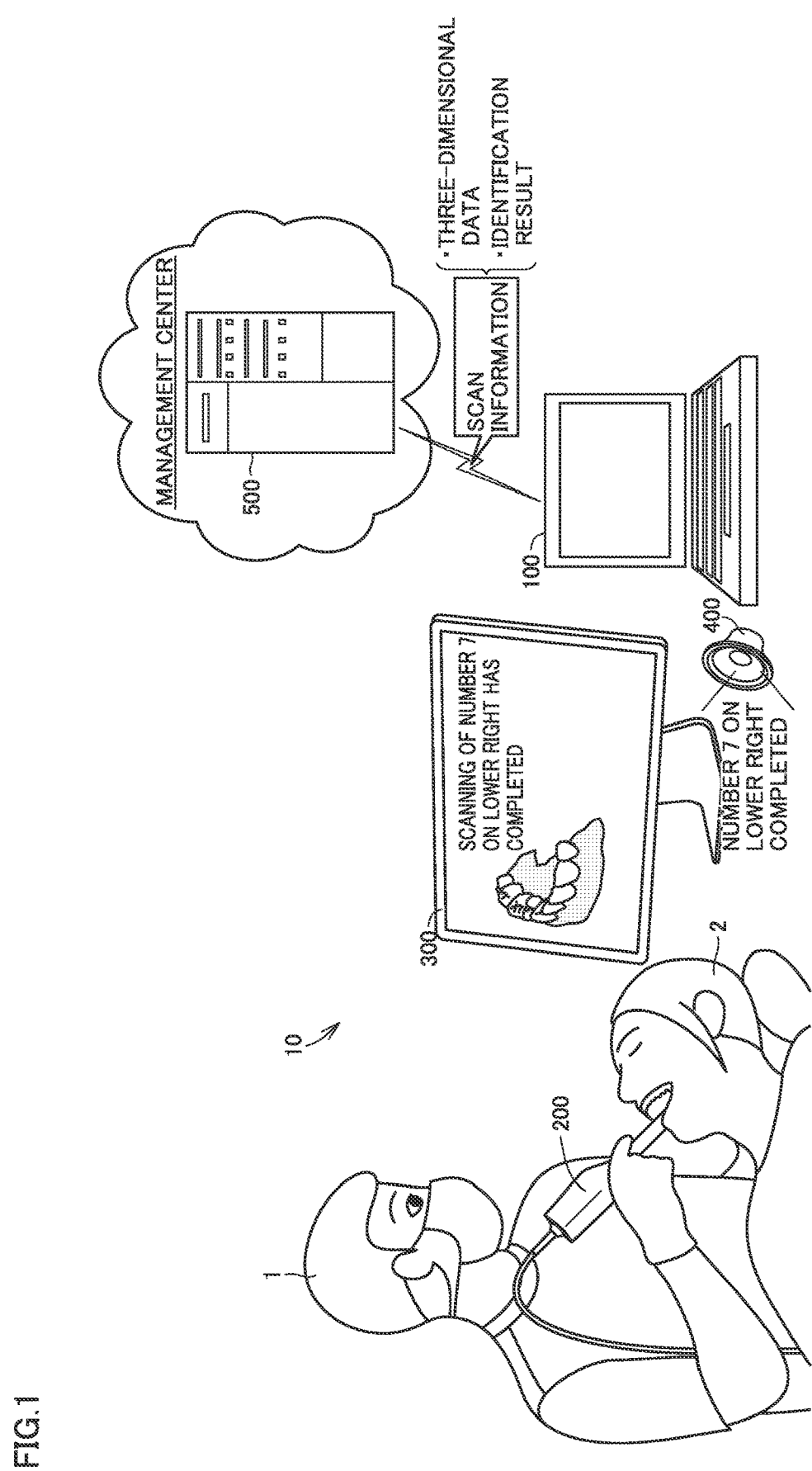
FIG. 1 is a schematic diagram showing an application example of an imaging support device according to the present first embodiment.

Embodiments of the present invention will be hereinafter described in detail with reference to the accompanying drawings, in which the same or corresponding components are denoted by the same reference characters, and the description thereof will not be repeated.

First Embodiment

Figure 2:
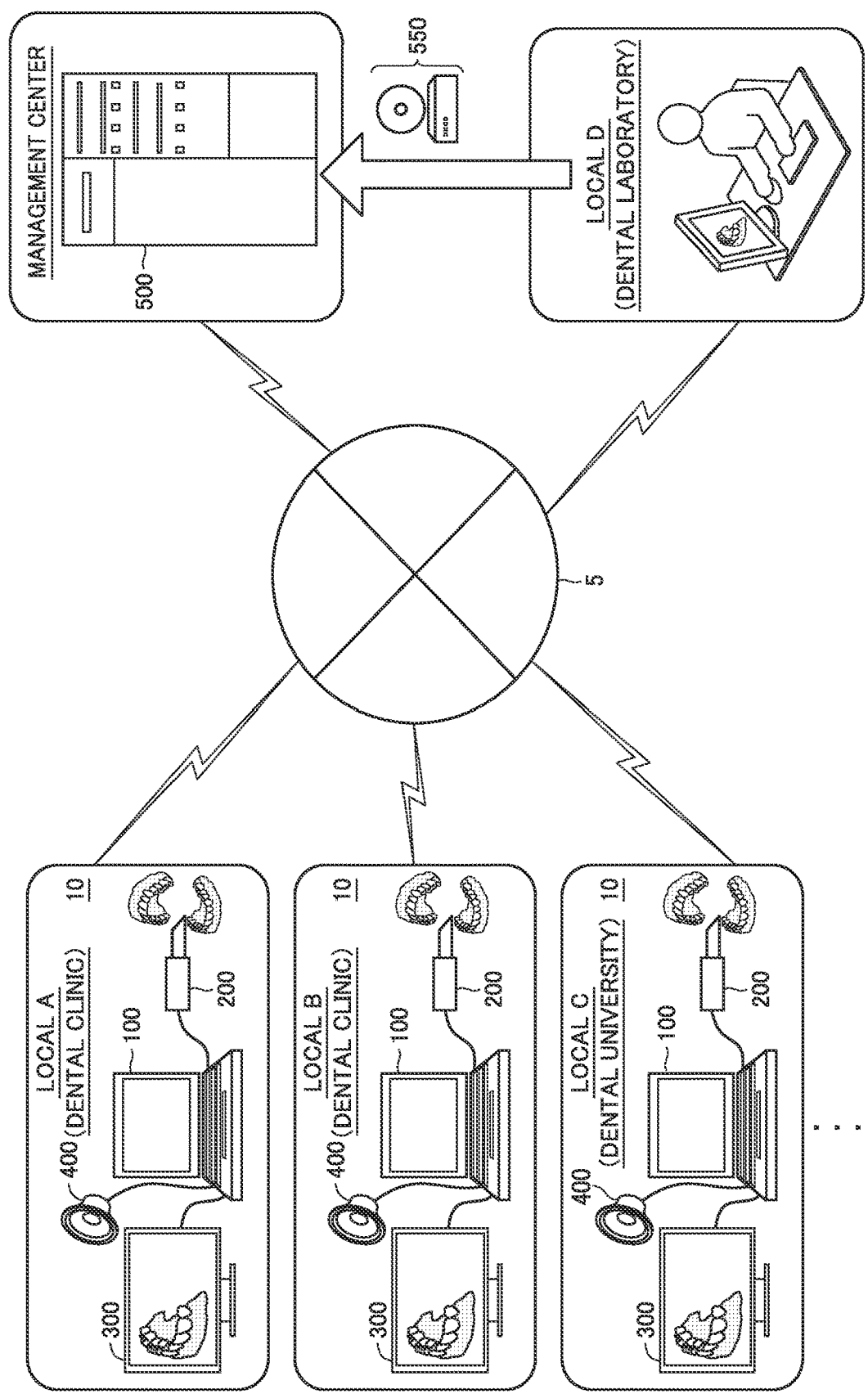
FIG. 2 is a schematic diagram showing an entire configuration of a scanner system according to the present first embodiment.

Referring to FIGS. 1 and 2, the following describes an example of a scanner system to which an imaging support device 100 according to the present first embodiment is applied. FIG. 1 is a schematic diagram showing an application example of imaging support device 100 according to the present first embodiment. FIG. 2 is a schematic diagram showing an entire configuration of a scanner system according to the present first embodiment.

As shown in FIG. 1, a user 1 images teeth inside an oral cavity with a scanner system 10, and thereby can acquire data of a three-dimensional shape (hereinafter also referred to as "three-dimensional data") including data of teeth of a subject 2. The "user" may be any person (a user) who uses scanner system 10, for example, an operator such as a dentist, a dental assistant, a teacher or a student of a dental university, a dental engineer, an engineer of a manufacturer, an operator in a manufacturing factory, and the like. The "subject" may be any person as a target of scanner system 10, such as a patient in a dental clinic or a subject in a dental university.

Scanner system 10 according to the present first embodiment includes a three-dimensional scanner 200, an imaging support device 100, a display 300, and a speaker 400. Three-dimensional scanner 200 acquires three-dimensional data by imaging a scan target with a built-in three-dimensional camera. Specifically, three-dimensional scanner 200 scans the inside of an oral cavity with an optical sensor or the like to acquire, as three-dimensional data, position information (coordinates of each of axes in the vertical direction, the horizontal direction, and the height direction) at each of a plurality of points forming a tooth to be scanned. Imaging support device 100 causes display 300 to show a three-dimensional image generated based on the three-dimensional data acquired by three-dimensional scanner 200.

For example, in order to digitally design a prosthesis or the like on a computer for filling a defect portion in a tooth of subject 2, user 1 uses three-dimensional scanner 200 to image the inside of the oral cavity of subject 2 to thereby acquire three-dimensional data of the inside of the oral cavity including teeth. Each time user 1 images the inside of the oral cavity, three-dimensional data is sequentially acquired and then a three-dimensional image of the inside of the oral cavity is shown on display 300. User 1 performs scanning so as to prevent excess and insufficiency in acquiring three-dimensional data while checking the three-dimensional image shown on display 300. At this time, based on the three-dimensional image obtained by visualization of the three-dimensional data including data of the teeth acquired by three-dimensional scanner 200, and also from the knowledge of user 1, user 1 identifies a type of the tooth that is being scanned or that has been completely scanned. However, since the level of knowledge is different for each user 1, the accuracy of the identification result may vary depending on the knowledge of user 1.

Thus, scanner system 10 according to the present first embodiment is configured to perform a process of automatically identifying a type of a tooth based on the three-dimensional data acquired by three-dimensional scanner 200 with the help of artificial intelligence (AI) included in imaging support device 100 to specify a type of a tooth as a target for imaging support. The process of identifying a type of a tooth using AI by imaging support device 100 will also be referred to as an "identification process".

A "type of a tooth" means a type of each of teeth such as: a central incisor, a lateral incisor, a canine, a first premolar, a second premolar, a first molar, a second molar, and a third molar on the right side in an upper jaw; a central incisor, a lateral incisor, a canine, a first premolar, a second premolar, a first molar, a second molar, and a third molar on the left side in the upper jaw; a central incisor, a lateral incisor, a canine, a first premolar, a second premolar, a first molar, a second molar, and a third molar on the right side in a lower jaw; and a central incisor, a lateral incisor, a canine, a first premolar, a second premolar, a first molar, a second molar, and a third molar on the left side in the lower jaw.

Specifically, when user 1 scans teeth inside the oral cavity of subject 2 using three-dimensional scanner 200, three-dimensional data including data of teeth is input into imaging support device 100. Imaging support device 100 performs an identification process of identifying a type of a tooth based on the input three-dimensional data including a feature of the tooth and an estimation model including a neural network.

The "estimation model" includes a neural network and a parameter used by the neural network, and is optimized (adjusted) when this "estimation model" is learned based on: the tooth information corresponding to the type of the tooth associated with the three-dimensional data; and an identification result about the type of the tooth that is obtained using the three-dimensional data. Specifically, when the three-dimensional data including data of teeth is input, the estimation model extracts a feature of the tooth by the neural network based on the three-dimensional data, and estimates a type of the tooth based on the extracted feature of the tooth. As to the estimation model, based on the comparison between the type of the tooth estimated by the estimation model and the type of the tooth (tooth information) associated with the input three-dimensional data, if the types match with each other, the parameter is not updated, whereas, if the types do not match with each other, the parameter is updated such that the types match with each other, thereby optimizing the parameter. In this way, the estimation model is learned by optimizing the parameter using teacher data including the three-dimensional data as input data and the type of the tooth (tooth information) as correct data.

Such a process of learning the estimation model will also be referred to as a "learning process". The estimation model optimized by the learning process will also be particularly referred to as a "learned model". In other words, in the present first embodiment, the estimation model before learning and the learned estimation model will be collectively referred to as an "estimation model", and particularly, the learned estimation model will also be referred to as a "learned model".

The "tooth information" includes names of teeth such as: a central incisor, a lateral incisor, a canine, a first premolar, a second premolar, a first molar, a second molar, and a third molar on the right side in an upper jaw; a central incisor, a lateral incisor, a canine, a first premolar, a second premolar, a first molar, a second molar, and a third molar on the left side in the upper jaw; a central incisor, a lateral incisor, a canine, a first premolar, a second premolar, a first molar, a second molar, and a third molar on the right side in a lower jaw; and a central incisor, a lateral incisor, a canine, a first premolar, a second premolar, a first molar, a second molar, and a third molar on the left side in the lower jaw. Further, the "tooth information" includes numbers assigned to respective teeth (for example, the tooth numbers generally used in the dental field) such as: number 1 assigned to a central incisor, number 2 assigned to a lateral incisor, number 3 assigned to a canine, number 4 assigned to a first premolar, number 5 assigned to a second premolar, number 6 assigned to a first molar, number 7 assigned to a second molar, and number 8 assigned to a third molar. In addition, the "tooth information" may include information of colors assigned to the respective teeth or information of symbols assigned to the respective teeth.

For example, when imaging support device 100 outputs, as imaging support, the information about the tooth that has been completely scanned (imaged), an identification process is performed using a learned model. Then, based on the identified type of the tooth, the type of the tooth as a target for imaging support is specified, and the specification result is output to display 300 and speaker 400.

Display 300 shows at least one of an image, a character, a numeral, an icon, and a symbol that correspond to the specification result. For example, when imaging support device 100 performs a support process of giving a notification about the type of the tooth that has been completely scanned, after three-dimensional scanner 200 completes scanning of the second molar corresponding to number 7 on the right side in the lower jaw, display 300 shows, as the specification result, an image indicating that scanning of the second molar corresponding to number 7 on the right side in the lower jaw has completed, for example, by showing a message such as "Scanning of number 7 on lower right has completed". When the specification result is incorrect, imaging support device 100 may accept the correction result through an operation input, an audio input, or the like. The audio input may be accepted by receiving a sound through a microphone (not shown).

Speaker 400 outputs a sound corresponding to the specification result. For example, after three-dimensional scanner 200 completes scanning of the second molar corresponding to number 7 on the right side in the lower jaw, speaker 400 adopts the specification result about the tooth obtained by imaging support device 100, and outputs a sound indicating that scanning of the second molar corresponding to number 7 on the right side in the lower jaw has completed, for example, by showing a message such as "Number 7 on lower right has completed". Also, imaging support device 100 does not output the type of the tooth that has been completely scanned to display 300, speaker 400, and the like, but may specify a type of a tooth that has been completely scanned, and then output the type of the tooth, which is to be scanned next, to display 300, speaker 400, and the like. When predicting a type of a tooth to be scanned next based on the information used for specifying the type of the tooth that has been completely scanned, imaging support device 100 predicts a type of a tooth that is not scanned and located close to the tooth of the type having been completely scanned, for example, as a type of a tooth to be scanned next. Further, imaging support device 100 may predict a type of a tooth to be scanned next, in combination with a motion sensor, a gyro sensor, or the like.

Further, the identification result obtained by the identification process performed by imaging support device 100 may be output together with the three-dimensional data used in the identification process, as scan information, to a dental laboratory and a server device 500 disposed in a management center. Imaging support device 100 may require user 1 to check the scan information when it outputs the scan information to the dental laboratory and server device 500 disposed in the management center.

For example, as shown in FIG. 2, scanner system 10 is disposed in each of a plurality of locals A to C. For example, locals A and B each are a dental clinic. In such a dental clinic, an operator or a dental assistant as user 1 uses scanner system 10 to acquire three-dimensional data including data of teeth of a patient as subject 2. Local C is a dental university, in which a teacher or a student as user 1 acquires three-dimensional data of the inside of the oral cavity of a target as subject 2. The scan information (three-dimensional data, identification result) acquired in each of locals A to C is output through a network 5 to a dental laboratory as a local and server device 500 disposed in a management center.

In the dental laboratory, based on the scan information acquired from each of locals A to C, a dental engineer or the like creates a prosthesis or the like for filling a defect portion in a tooth of subject 2. In the management center, server device 500 stores an accumulation of the scan information acquired from each of locals A to C, and holds the stored information as big data.

It should be noted that server device 500 does not necessarily have to be disposed in a management center different from a local in which the dental clinic is disposed, but may be disposed in a local. For example, server device 500 may be disposed in any one of locals A to C. Further, a plurality of imaging support devices 100 may be disposed in one local. Also, server device 500 capable of communicating with the plurality of imaging support devices 100 may be disposed in this one local. Further, server device 500 may be implemented in the form of a cloud service.

In a dental laboratory, scan information is aggregated from various locations such as locals A to C. Thus, the scan information held in the dental laboratory may be transmitted to the management center through network 5, or may be transmitted to the management center through a removable disk 550 such as a compact disc (CD) and a universal serial bus (USB) memory.

In addition, the scan information may be sent to the management center also from each of locals A to C through removable disk 550 without through network 5. Further, the scan information may be exchanged also among locals A to C through network 5 or removable disk 550.

Imaging support device 100 in each of locals A to C holds an estimation model, and uses the holding estimation model to identify a type of a tooth during the identification process. Imaging support devices 100 in locals A to C learn their respective estimation models by their respective learning processes to generate learned models. Further, in the present first embodiment, server device 500 also holds an estimation model. Server device 500 learns the estimation model by the learning process performed using the scan information acquired from imaging support device 100 in each of locals A to C and from the dental laboratory, to thereby generate a learned model and then distribute the learned model to imaging support device 100 in each of locals A to C. In the present first embodiment, each of imaging support devices 100 in locals A to C and server device 500 performs the learning process, but only each of imaging support devices 100 in locals A to C may perform the learning process, or only server device 500 may perform the learning process. In the case where only server device 500 performs the learning process, the estimation model (learned model) held by imaging support device 100 in each of locals A to C is shared among imaging support devices 100 in locals A to C.

Further, server device 500 may have functions of the identification process and the specification process in imaging support device 100. For example, each of locals A to C may transmit the acquired three-dimensional data to server device 500. Then, server device 500 may calculate the identification result about the type of the tooth in each three-dimensional data received from each of local areas A to C based on the three-dimensional data, or may specify a type of a tooth as a target for imaging support based on the identified type of the tooth. Then, server device 500 may transmit the identification results and the specification results to their respective locals A to C. Then, locals A to C each may specify a type of a tooth as a target for imaging support based on the identification result received from server device 500 or may output the specification results to their respective displays or the like. In this way, each of locals A to C and server device 500 may be configured in the form of a cloud service. In this way, server device 500 only has to hold the estimation model (learned model), and thereby, each of locals A to C can obtain the identification result without having to hold the estimation model (learned model).

In this way, according to scanner system 10 of the present first embodiment, the AI included in imaging support device 100 is used to automatically identify a type of a tooth based on the three-dimensional data acquired by three-dimensional scanner 200 and specify a type of a tooth as a target for imaging support based on the identified type of the tooth. By using the AI, the feature of a tooth obtained from the knowledge of user 1 can be found. Further, the feature of a tooth that cannot be extracted by user 1 can also be found. Thereby, user 1 can accurately identify a type of a tooth without relying on his/her own knowledge. Imaging support device 100 uses the identification result, for example, to perform imaging support for specifying a type of a tooth that has been completely imaged, thereby allowing user 1 to easily recognize the correspondence between the tooth that has been completely imaged and the type of the tooth.

[Hardware Configuration of Imaging Support Device]

Figure 3:
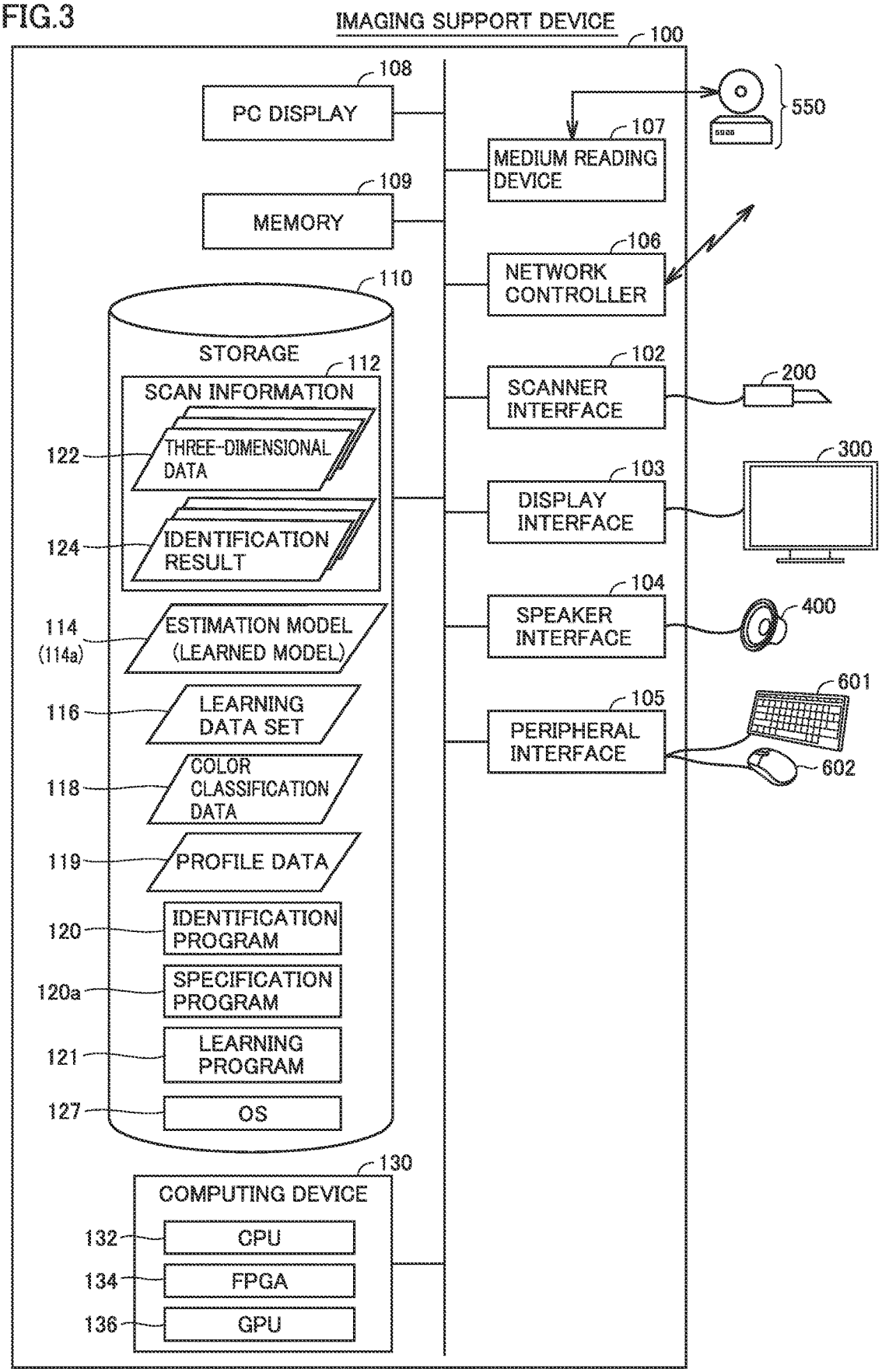
FIG. 3 is a schematic diagram showing a hardware configuration of the imaging support device according to the present first embodiment.

An example of a hardware configuration of imaging support device 100 according to the present first embodiment will be hereinafter described with reference to FIG. 3. FIG. 3 is a schematic diagram showing a hardware configuration of imaging support device 100 according to the present first embodiment. Imaging support device 100 may be implemented, for example, by a general-purpose computer or a computer dedicated to scanner system 10.

As shown in FIG. 3, imaging support device 100 includes, as main hardware elements, a scanner interface 102, a display interface 103, a speaker interface 104, a peripheral interface 105, a network controller 106, a medium reading device 107, a PC display 108, a memory 109, a storage 110, and a computing device 130.

Scanner interface 102, which is an interface for connecting three-dimensional scanner 200, implements input/output of data between imaging support device 100 and three-dimensional scanner 200.

Display interface 103, which is an interface for connecting display 300, implements input/output of data between imaging support device 100 and display 300. Display 300 is configured, for example, by a liquid crystal display (LCD), an organic electroluminescence (ELD) display or the like.

Speaker interface 104, which is an interface for connecting speaker 400, implements input/output of data between imaging support device 100 and speaker 400.

Peripheral interface 105, which is an interface for connecting peripheral devices such as a keyboard 601 and a mouse 602, implements input/output of data between imaging support device 100 and each peripheral device.

Network controller 106 transmits and receives data through network 5 to and from each of: a device disposed in the dental laboratory; server device 500 disposed in the management center; and other imaging support devices 100 disposed in other locals. Network controller 106 supports optional communication schemes such as Ethernet (registered trademark), a wireless local area network (LAN), or Bluetooth (registered trademark).

Medium reading device 107 reads various pieces of data such as scan information stored in removable disk 550.

PC display 108 is a display dedicated to imaging support device 100. PC display 108 is configured by an LCD or an organic EL display, for example. In the present first embodiment, PC display 108 is provided separately from display 300 but may be integrated with display 300.

Memory 109 provides a storage area in which program codes, work memory, and the like are temporarily stored when computing device 130 executes an optional program. Memory 109 is configured by a volatile memory device such as a dynamic random access memory (DRAM) or a static random access memory (SRAM), for example.

Storage 110 provides a storage area in which various pieces of data required for the identification process, the learning process, and the like are stored. Storage 110 is configured by a non-volatile memory device such as a hard disk or a solid state drive (SSD), for example.

Storage 110 stores scan information 112, an estimation model 114 (a learned model 114a), a learning data set 116, color classification data 118, profile data 119, an identification program 120, a learning program 121, and an operating system (OS) 127.

Scan information 112 includes three-dimensional data 122 acquired by three-dimensional scanner 200, and an identification result 124 obtained by the identification process performed based on three-dimensional data 122. Identification result 124 is associated with three-dimensional data 122 used in the identification process and is stored in storage 110. Learning data set 116 is a group of learning data used for the learning process of estimation model 114. Color classification data 118 is data used for generation of learning data set 116 and the learning process. Profile data 119 is attribute information related to subject 2 and includes a summary of profiles about subject 2 (for example, information on medical charts) such as an age, a gender, a race, a height, a weight, and a place of residence. Identification program 120 is a program for performing the identification process. A specification program 120a is a program for performing the specification process of specifying a type of a tooth as a target for imaging support. Learning program 121 is a program for performing the learning process of estimation model 114, and also includes a program for performing the identification process.

Computing device 130 is a computing entity that executes various programs to thereby perform various processes such as an identification process and a learning process. Computing device 130 is also one example of a computer. Computing device 130 is configured, for example, by a central processing unit (CPU) 132, a field-programmable gate array (FPGA) 134, a graphics processing unit (GPU) 136, and the like.

[Hardware Configuration of Server Device]

Figure 4:
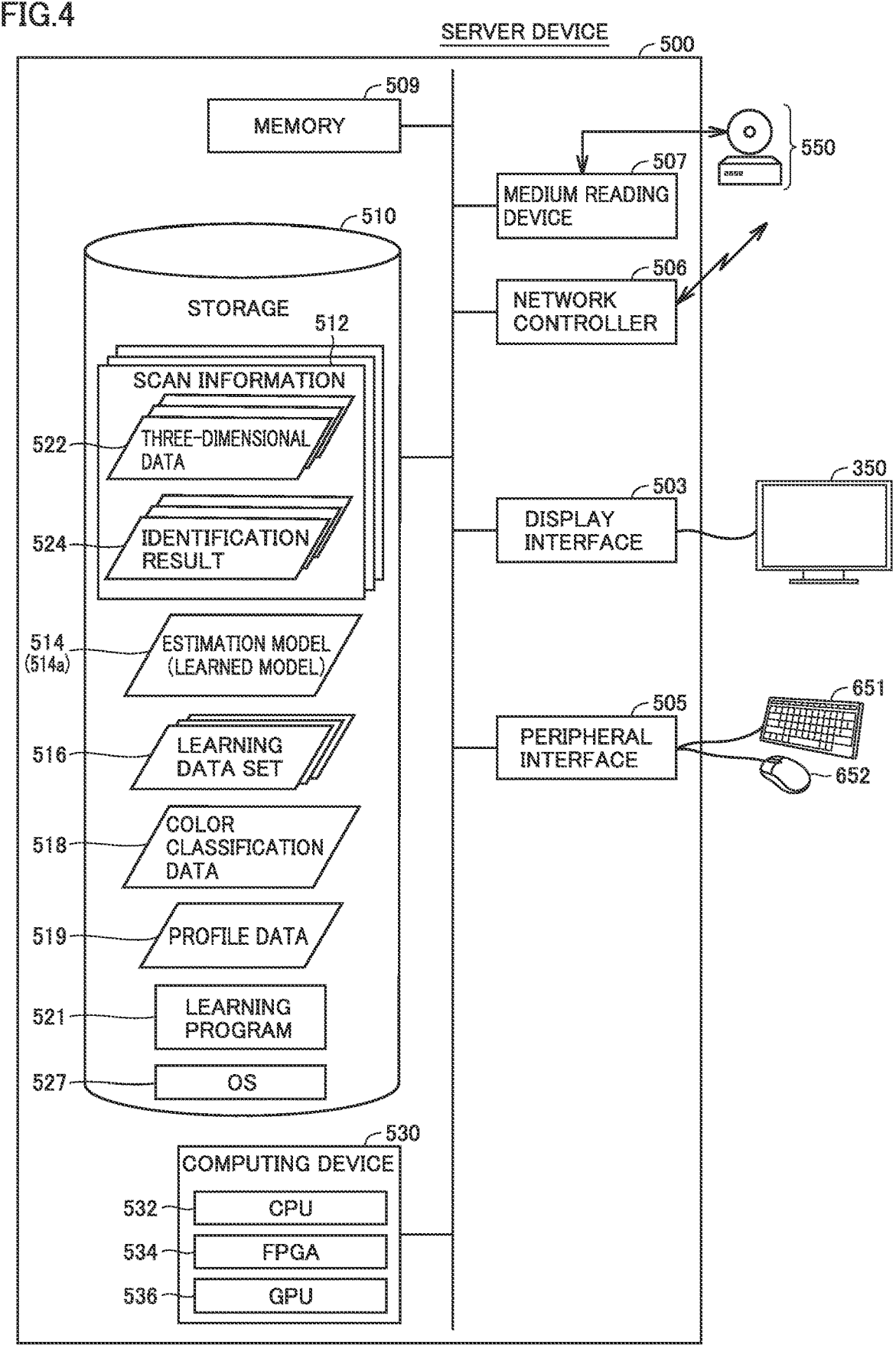
FIG. 4 is a schematic diagram showing a hardware configuration of a server device according to the present first embodiment.

An example of a hardware configuration of server device 500 according to the present first embodiment will be hereinafter described with reference to FIG. 4. FIG. 4 is a schematic diagram showing a hardware configuration of server device 500 according to the present first embodiment. Server device 500 may be implemented, for example, by a general-purpose computer or by a computer dedicated to scanner system 10.

As shown in FIG. 4, server device 500 includes, as main hardware elements, a display interface 503, a peripheral interface 505, a network controller 506, a medium reading device 507, a memory 509, a storage 510, and a computing device 530.

Display interface 503, which is an interface for connecting display 350, implements input/output of data between server device 500 and display 350. Display 350 is configured, for example, by an LCD, an organic ELD display, or the like.

Peripheral interface 505, which is an interface for connecting peripheral devices such as a keyboard 651 and a mouse 652, implements input/output of data between server device 500 and each peripheral device.

Network controller 506 transmits and receives data through network 5 to and from each of imaging support device 100 disposed in each local and a device disposed in a dental laboratory. Network controller 506 may support optional communication schemes such as Ethernet (registered trademark), a wireless LAN, or Bluetooth (registered trademark).

Medium reading device 507 reads various pieces of data such as scan information stored in removable disk 550.

Memory 509 provides a storage area in which program codes, work memory, and the like are temporarily stored when computing device 530 executes an optional program. Memory 509 is configured, for example, by a volatile memory device such as a DRAM or an SRAM.

Storage 510 provides a storage area in which various pieces of data required for the learning process and the like is stored. Storage 510 is configured, for example, by a non-volatile memory device such as a hard disk or an SSD.

Storage 510 stores scan information 512, an estimation model 514 (a learned model 514a), a learning data set 516, color classification data 518, profile data 519, a learning program 521, and an OS 527.

Scan information 512 includes: three-dimensional data 522 acquired through network 5 from imaging support device 100 and a dental laboratory disposed in locals; and an identification result 524 obtained by an identification process performed based on three-dimensional data 522. Identification result 524 is associated with three-dimensional data 522 used in the identification process and is stored in storage 510. Learning data set 516 is a group of learning data used for the learning process of estimation model 514. Color classification data 518 is data used for generation of learning data set 516 and the learning process. Profile data 519 is attribute information related to subject 2 and includes a summary of profiles about subject 2 (for example, information on medical charts) such as an age, a gender, a race, a height, a weight, and a place of residence. Learning program 521 is a program for performing the learning process of estimation model 514, and also includes a program for performing the identification process.

In addition, estimation model 514 (learned model 514a) is transmitted to imaging support device 100 in each local, and thereby, held as estimation model 114 (learned model 114a) by imaging support device 100.

Computing device 530 is a computing entity that executes various programs to thereby perform various processes such as a learning process. Computing device 530 is also one example of a computer. Computing device 530 is configured, for example, by a CPU 532, an FPGA 534, a GPU 536, and the like.

[Specification Process by Imaging Support Device]

Figure 5:
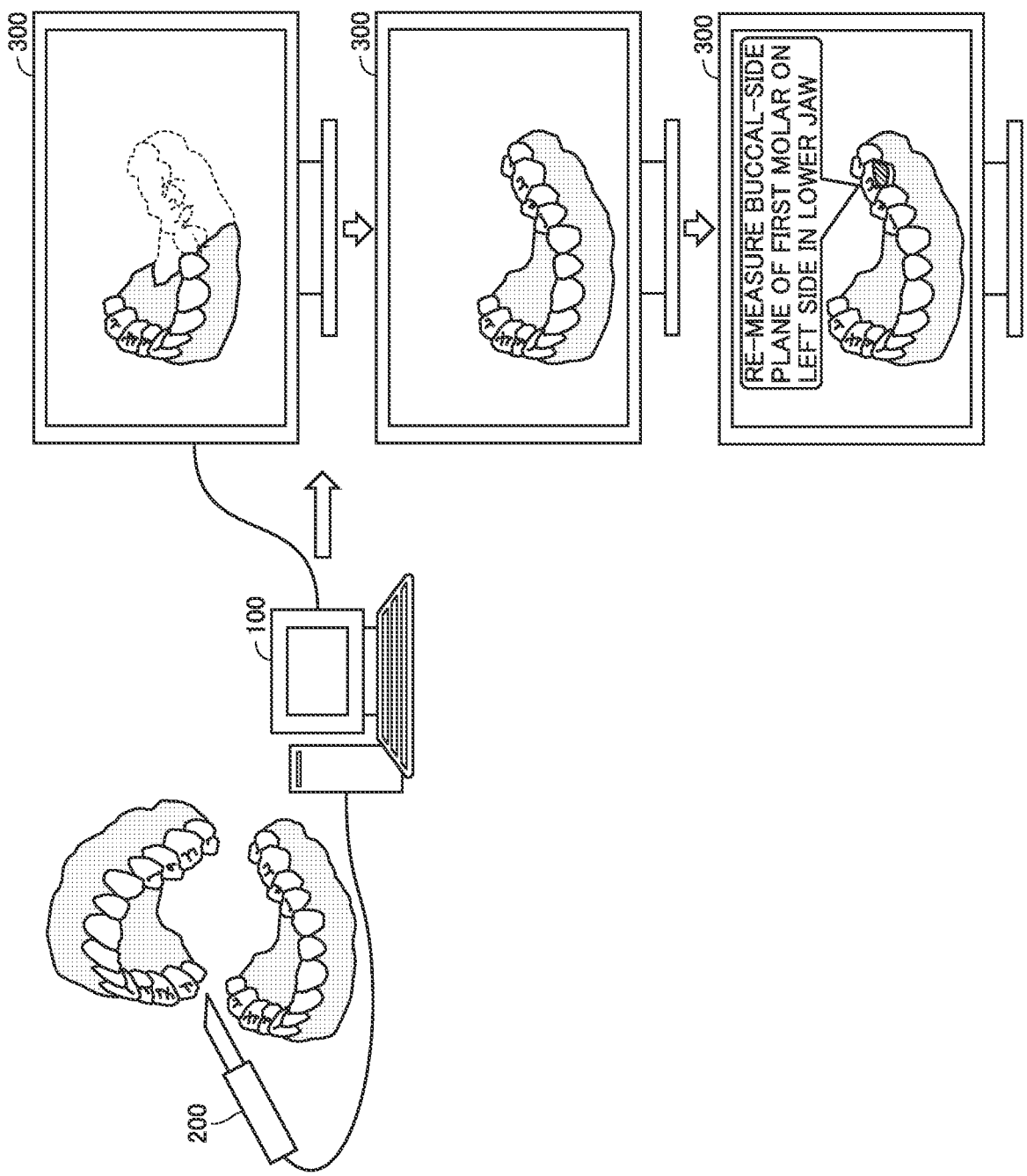
FIG. 5 is a schematic diagram showing a manner of use of the imaging support device according to the present first embodiment.

The following describes an example of an imaging support device in accordance with imaging support device 100 according to the present first embodiment with reference to FIGS. 5 to 8. FIG. 5 is a schematic diagram showing a manner of use of imaging support device 100 according to the present first embodiment. The following describes the case of supporting three-dimensional scanner 200 (scanning device) that acquires three-dimensional data of a dental arch by joining a plurality of pieces of three-dimensional data acquired by scanning (imaging) the inside of an oral cavity. Of course, three-dimensional scanner 200 may be a device that scans the inside of the oral cavity to acquire a plurality of pieces of three-dimensional data of some portions of a dentition without joining the plurality of pieces of three-dimensional data.

Three-dimensional scanner 200 scans the inside of the oral cavity as shown in FIG. 5 and thereby can sequentially acquire pieces of three-dimensional data of some portions of the dental arch. Then, by joining these pieces of three-dimensional data, three-dimensional data of the entire dental arch can be acquired. However, when three-dimensional scanner 200 is used to scan the inside of the oral cavity to acquire three-dimensional data of the dental arch, an overlapping area, a defect area, and the like may exist in the plurality of pieces of imaged three-dimensional data depending on the user's operation.

Thus, at the timing at which the entire dental arch is imaged, imaging support device 100 specifies a lacking portion (defect area) of a tooth for which the information obtained from the three-dimensional data does not satisfy a prescribed criterion, and then, outputs the specification result to display 300 as support information. In other words, as shown in FIG. 5, imaging support device 100 puts a marking on the tooth having a lacking portion and outputs a message of "re-measure buccal-side plane of first molar on left side in lower jaw" to display 300, for implementing imaging support. Thus, by the output of imaging support device 100, user 1 can easily, quickly and accurately perform re-scanning with three-dimensional scanner 200. In this case, the prescribed criterion is a criterion at which the amount of data is predetermined with the degree of accuracy required to create a prosthesis from the three-dimensional data acquired by three-dimensional scanner 200.

In FIG. 5, imaging support device 100 specifies the type of the tooth lacking three-dimensional data as "buccal-side plane of first molar on left side in lower jaw" or the like, and thus, specifies not only the type of the tooth but also a partial area in the tooth. Of course, imaging support device 100 may specify only the type of the tooth lacking three-dimensional data, for example, only the "first molar on left side in lower jaw".

Figure 6:
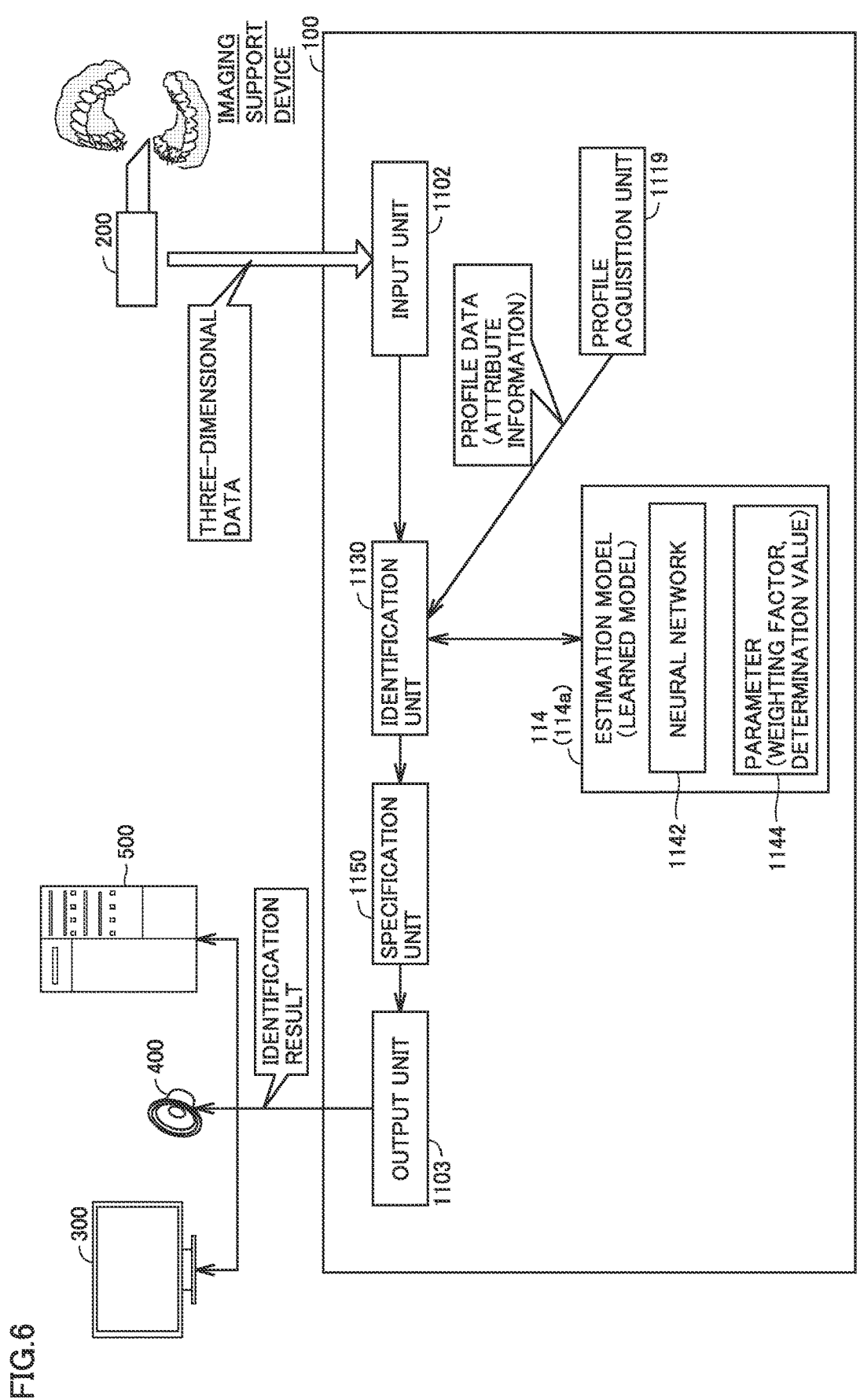
FIG. 6 is a schematic diagram showing a functional configuration of the imaging support device according to the present first embodiment.
Figure 7:
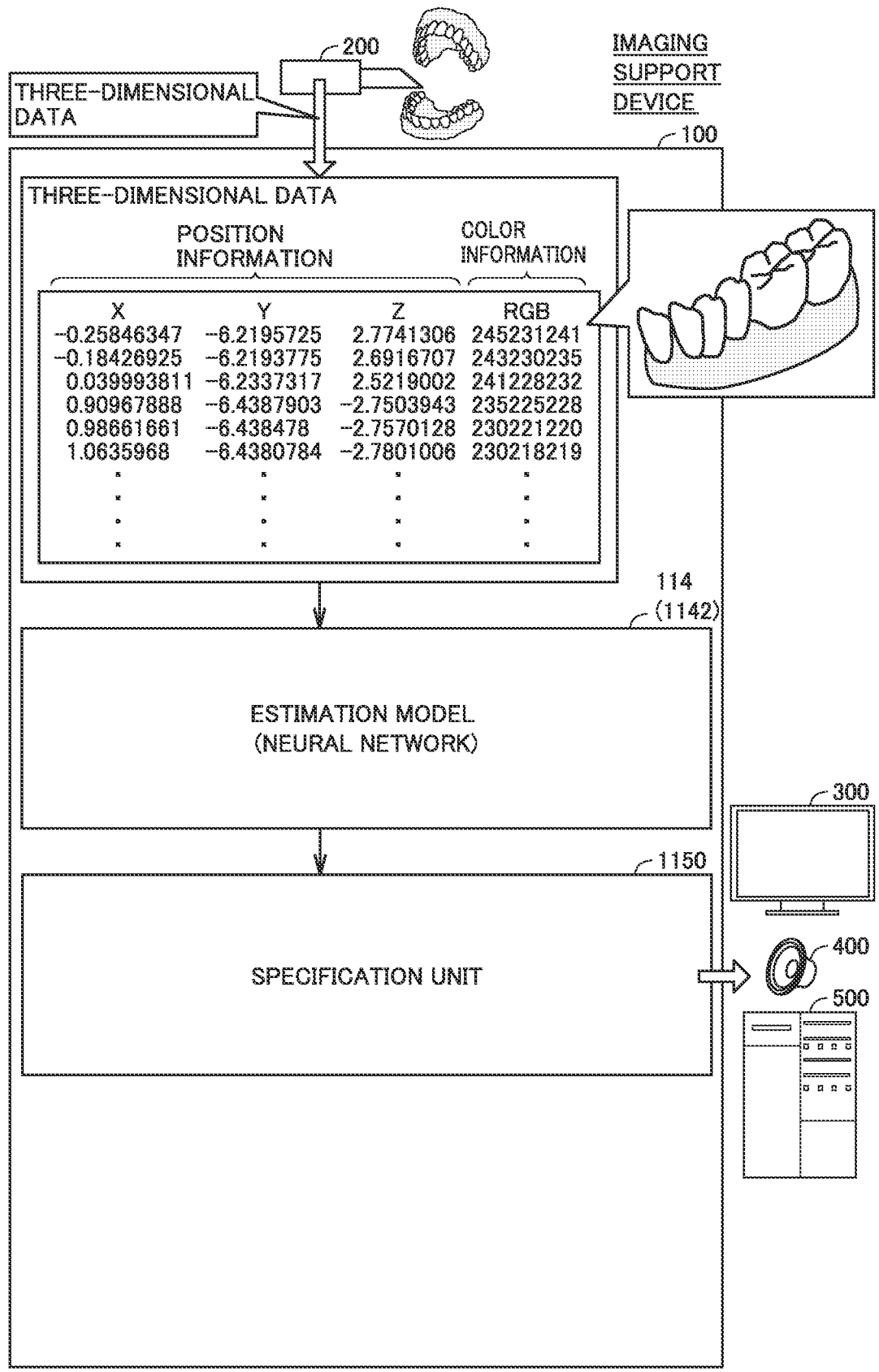
FIG. 7 is a schematic diagram for illustrating an identification process by the imaging support device according to the present first embodiment.

FIG. 6 is a schematic diagram showing a functional configuration of imaging support device 100 according to the present first embodiment. FIG. 7 is a schematic diagram for illustrating the identification process by imaging support device 100 according to the present first embodiment. FIG. 8 is a schematic diagram showing examples of teeth to be identified in the identification process according to the present first embodiment. In FIG. 8, teeth to be scanned by three-dimensional scanner 200 are represented by diagrammatic drawings.

As shown in FIG. 6, imaging support device 100 includes an input unit 1102, a profile acquisition unit 1119, an identification unit 1130, a specification unit 1150, and an output unit 1103, each of which is provided as a functional unit related to the identification process and the specification process. Each of these functions is implemented by computing device 130 of imaging support device 100 executing an OS 127, identification program 120, and specification program 120a.

Input unit 1102 receives three-dimensional data acquired by three-dimensional scanner 200. Profile acquisition unit 1119 acquires profile data 119 of subject 2. Based on the three-dimensional data input into input unit 1102 and profile data 119 of subject 2 acquired by profile acquisition unit 1119, identification unit 1130 performs an identification process of identifying a type of a tooth using estimation model 114 (learned model 114a).

Estimation model 114 includes a neural network 1142 and a parameter 1144 used by neural network 1142. Parameter 1144 includes a weighting factor used for calculation by neural network 1142 and a determination value used for determination of identification. From among teeth that need to be imaged for user 1, specification unit 1150 specifies a type of a tooth for which information obtained from a tooth image (for example, three-dimensional data) does not satisfy a prescribed criterion. Specifically, based on the type of the tooth identified by identification unit 1130, specification unit 1150 specifies a type of a tooth corresponding to a portion of the acquired three-dimensional data that does not exceed a predetermined amount of data. Also, specification unit 1150 does not necessarily have to specify a type of a tooth for which data is insufficient, but also may specify other types of teeth such as a type of a tooth to be imaged next, or a type of a tooth at the time when imaging is stopped. Output unit 1103 outputs the specification result obtained by specification unit 1150 to display 300, speaker 400, and the like.

In this case, as shown in FIG. 7, the three-dimensional data input into input unit 1102 includes three-dimensional position information at each of points of a tooth and color information at each of points of a tooth. In the identification process, the position information is used. The position information includes coordinates of an absolute position in three dimensions with respect to a predetermined position. For example, the position information includes coordinates of an absolute position on each of axes including an X axis (for example, an axis of a tooth in the horizontal direction), a Y axis (for example, an axis of a tooth in the vertical direction), and a Z axis (for example, an axis of a tooth in the height direction) with reference to a central position at each of points of a tooth as an origin point. The position information is not limited to the coordinates of an absolute position in three dimensions with respect to a predetermined position, but may include coordinates of a relative position in three dimensions indicating the distance from an adjacent point, for example.

In this case, as shown in FIG. 8, when the tooth to be scanned by three-dimensional scanner 200 is an incisor in an upper jaw, user 1 scans the inside of the oral cavity of subject 2 such that the three-dimensional image to be obtained includes at least an image of an area on the upper lip side, an image of an area on the palate side, and an image of an area on the incisal edge side. When the teeth to be scanned by three-dimensional scanner 200 are a canine and a molar in the upper jaw, user 1 scans the inside of the oral cavity of subject 2 such that the three-dimensional image to be obtained includes at least an image of an area on the buccal side, an image of an area on the palate side, and an image of an occlusion area. When the tooth to be scanned by three-dimensional scanner 200 is an incisor in the lower jaw, user 1 scans the inside of the oral cavity of subject 2 such that the three-dimensional image to be obtained includes at least an image of an area on the lower lip side, an image of an area on the tongue side, and an image of an area on the incisal edge side. When the teeth to be scanned by three-dimensional scanner 200 are a canine and a molar in the lower jaw, user 1 scans the inside of the oral cavity of subject 2 such that the three-dimensional image to be obtained includes at least an image of an area on the buccal side, an image of an area on the tongue side, and an image of an occlusion area.

In general, the teeth of subject 2 vary in shape and size depending on their types. For example, in the case of an incisor in the upper jaw, the plane on the upper lip side generally has a U-shape. In the case of a canine in the upper jaw, the plane on the buccal side generally has a pentagonal shape. Each tooth has a characteristic shape and a characteristic size depending on its type. Based on the three-dimensional data obtained by digitizing such a characteristic shape and a characteristic size, identification unit 1130 uses estimation model 114 to identify a type of a tooth corresponding to the three-dimensional data.

As shown in FIG. 7, estimation model 114 includes neural network 1142. In neural network 1142, a value of the position information included in the three-dimensional data input into input unit 1102 is input to an input layer. Then, in neural network 1142, for example, by the intermediate layer, the input value of the position information is multiplied by a weighting factor, and a predetermined bias is added to the input value of the position information, and also, calculation with a predetermined function is performed. Then, the calculation result is compared with the determination value. Further, in neural network 1142, the result obtained by the above-mentioned calculation and determination is output as the identification result from the output layer. The calculation and determination by neural network 1142 may be performed by any method as long as a tooth can be identified based on the three-dimensional data.

In neural network 1142 of estimation model 114, the intermediate layer has a multi-layered structure, and thus, a process by deep learning is performed. In the present embodiment, examples of identification program 120 for performing an identification process specialized for a three-dimensional image may be VoxNet, 3D ShapeNets, Multi-View CNN, RotationNet, OctNet, FusionNet, PointNet, PointNet++, SSCNet, MarrNet, and the like, but other programs may be used. An existing mechanism may also be applied to neural network 1142.

In such a configuration, when imaging support device 100 receives three-dimensional data corresponding to a three-dimensional image including a plurality of teeth, imaging support device 100 can extract respective features of the teeth using neural network 1142 of estimation model 114 based on the three-dimensional data, and then identify respective types of the teeth based on the extracted features of the teeth. Further, as shown in FIG. 7, imaging support device 100 receives not only a target tooth to be identified but also three-dimensional data including data of teeth adjacent to this target tooth, and thereby, neural network 1142 of estimation model 114 can extract the feature of the target tooth also in consideration of the relation with the shapes of the adjacent teeth. Imaging support device 100 can extract not only a tooth feature that is generally recognized but also a tooth feature that is not generally recognized, and thereby, can accurately identify a type of a tooth.

The neural network included in estimation model 514 held in server device 500 has the same configuration as that of neural network 1142 included in estimation model 114 shown in FIG. 7.

[Generation of Learning Data]

An example of generation of learning data set 116 will be hereinafter described. First, three-dimensional data is acquired by three-dimensional scanner 200. The three-dimensional data includes three-dimensional position information at each of points of a corresponding tooth and color information (RGB values) at each of points of the tooth. When a three-dimensional image is generated based on the three-dimensional data acquired by three-dimensional scanner 200, a three-dimensional image including teeth in actual colors is generated.

Then, a noise removing process is performed as a preparation for a color-coding process for each tooth. For example, in the present first embodiment, a three-dimensional image corresponding to the three-dimensional data is gray-scaled. Then, predetermined colors are applied to the respective teeth included in the three-dimensional image corresponding to the three-dimensional data, and thereby, the teeth are color-coded. For example, color classification data 118 held in imaging support device 100 is provided for each of areas inside the oral cavity, such as the left side in the lower jaw, the right side in the lower jaw, the left side in the upper jaw, and the right side in the upper jaw.

For example, the second molar is assigned number 7 as a tooth number and assigned red as color information. The first molar is assigned number 6 as a tooth number and assigned green as color information. The second premolar is assigned number 5 as a tooth number and assigned blue as color information. In this way, in each color classification data 118, the tooth number and the color information are assigned in advance for each type of tooth.

Application of colors to the respective teeth is performed by user 1 (such as an engineer of a manufacturer or an operator in a manufacturing factory). Specifically, user 1 identifies a type of each tooth included in the three-dimensional image based on his/her knowledge, specifies colors corresponding to the identified types of teeth while referring to color classification data 118, and then, applies the specified colors to the images of the respective teeth.

For example, when user 1 identifies the tooth included in the three-dimensional image as the second molar, user 1 applies a red color to an image of the tooth. When user 1 identifies the tooth included in the three-dimensional image as the first molar, user 1 applies a green color to an image of the tooth.

Further, in accordance with the color-coding of the teeth, the color information (RGB values) at each point of each of the teeth corresponding to the three-dimensional data is changed to a value corresponding to the color applied to each tooth. For example, the color information (RGB values) is "255000000" for each position coordinate of the second molar in red color; the color information (RGB values) is "000255000" for each position coordinate of the first molar in green color; and the color information (RGB values) is "00000255" for each position coordinate of the second premolar in blue color. In other words, predetermined color information (RGB values) is associated with each of points of a tooth corresponding to the three-dimensional data.

When the predetermined color information is associated with each tooth, the three-dimensional data includes position information and color information that corresponds to the applied color. Then, such three-dimensional data is employed as learning data. In other words, in the learning data according to the present embodiment, the color information corresponding to each type of tooth is associated (labeled) with the position information referred to in the identification process. Further, the color information is associated with the three-dimensional data such that the range of each of the teeth corresponding to the three-dimensional data can be specified. Specifically, the same color information is associated for each position information corresponding to each tooth. A collection of such learning data is held in imaging support device 100 as learning data set 116.

Thus, when generating learning data, user 1 applies colors to the respective teeth included in the three-dimensional image to thereby label the correct data, which provides many advantages. For example, in the case of labeling with simple characters or symbols, it is difficult for user 1 to recognize the range of each tooth. However, in the case of labeling by color-coding, application of colors allows user 1 to readily recognize the boundary between a target tooth to be labeled and a tooth adjacent to the target tooth, and the boundary between a target tooth to be labeled and gums. Further, user 1 applies colors while checking the three-dimensional image from various angles during labeling. Even when the angle at which the image is viewed is changed, user 1 still readily recognizes a specific range in which application of colors to the teeth that are being labeled has completed.

In the present embodiment, based on the knowledge of user 1, user 1 manually applies colors to the respective teeth included in the three-dimensional image. However, such a manual operation can also be partially performed complementarily by software. For example, the boundary between a target tooth to be labeled and a tooth adjacent to the target tooth and the boundary between a target tooth to be labeled and gums may be specified by edge detection, which allows extraction of only the target tooth to be labeled.

Further, generation of learning data set 116 is also applicable to generation of learning data set 516 held in server device 500. For example, learning data set 116 may be applied to learning data set 516 held in server device 500, or color classification data 118 may be applied to color classification data 518 held in server device 500.

[Generation of Learned Model]

An example of generation of learned model 114a will be hereinafter described. Learning data set 116 can be classified for each category based on the profile of subject 2 as a target to be scanned when learning data set 116 is generated. For example, the learning data sets generated from the three-dimensional data including data of teeth of applicable subject 2 can be assigned to an age (minors, adults, elderly people), a gender (males, females), a race (Asians, Europeans, Africans), a height (less than 150 cm, 150 cm or more), a weight (less than 50 kg, 50 kg or more), and a place of residence (residing in Japan, residing in regions other than Japan). The layers of the respective categories can be set as appropriate. For example, ages can be stratified in greater detail for each prescribed age difference (in this case, for each 3 years of age), specifically for age 0 to age 3, age 4 to age 6, age 7 to age 9, and the like.

Imaging support device 100 generates learned model 114a by learning estimation model 114 using a plurality of learning data sets 116 that can be classified for each category. There may be an overlap among the pieces of learning data depending on how the categories are classified. In the case where there is an overlap among the pieces of learning data, only one piece of learning data has to be used for learning of estimation model 114.

In general, a tooth shape varies in feature depending on genetics or living environments such as an age, a gender, a race, a height, a weight, and a place of residence. For example, in general, permanent teeth of an adult are larger than primary teeth of a child, and also, permanent teeth are different in shape from primary teeth. In general, male teeth are larger than female teeth, and also, male teeth are different in shape from female teeth. In general, European teeth tend to be pointed at their tips so as to allow the Europeans to easily bite off hard meat and bread, whereas Japanese teeth tend to be smooth at their tips so as to allow the Japanese to easily mash soft rice and vegetables. Accordingly, the learning process is performed based on the profile data as in the present embodiment, to thereby allow generation of a learned model that allows identification of a type of a tooth in consideration of genetics, living environments or the like.

It should be noted that generation of learned model 114a is also applicable to generation of learned model 514a held in server device 500. For example, learning data set 116 may be applied to learning data set 516 held in server device 500, or estimation model 114 may be applied to estimation model 514 held in server device 500.

[Learning Process of Identification Unit]

The learning process performed by imaging support device 100 will be hereinafter described. The learning process is implemented by computing device 130 of imaging support device 100 executing OS 127 and learning program 121. From learning data set 116, imaging support device 100 selects learning data to be used for learning. Imaging support device 100 inputs, into estimation model 114, the position information of the three-dimensional data included in the selected learning data and the profile data of subject 2 as a target to be scanned during generation of the learning data. At this time, the correct data labeled in the three-dimensional data is not input into imaging support device 100. Based on the feature of a tooth corresponding to the three-dimensional data, imaging support device 100 performs an identification process of identifying a type of the tooth using estimation model 114. In the identification process, imaging support device 100 identifies a type of the tooth using estimation model 114 based on the profile data in addition to the three-dimensional data.

Imaging support device 100 updates parameter 1144 of estimation model 114 based on the error between the identification result about the type of the tooth identified by the identification process and the correct data corresponding to the learning data used in the learning process.

For example, as a result of the identification based on the position information of a specific tooth, imaging support device 100 estimates color information corresponding to this specific tooth. Imaging support device 100 compares the color information (correct data) corresponding to the specific tooth included in the learning data with the color information estimated by imaging support device 100 itself. Then, when these pieces of color information match with each other, imaging support device 100 maintains parameter 1144 of estimation model 114. In contrast, when these pieces of color information do not match with each other, imaging support device 100 updates parameter 1144 of estimation model 114 such that these pieces of color information match with each other.

Alternatively, as a result of the identification based on the position information of a specific tooth, imaging support device 100 estimates color information corresponding to this specific tooth, and specifies the type of the tooth and the number of the tooth (the correct data) that correspond to the color information based on color classification data 118. Imaging support device 100 compares the type of the tooth and the number of the tooth (the correct data) that are assigned to the color information corresponding to the specific tooth included in the learning data with the type of the tooth and the number of the tooth that are estimated by imaging support device 100 itself. Then, when the types match with each other and the numbers match with each other, imaging support device 100 maintains parameter 1144 of estimation model 114. When the types do not match with each other and the numbers do not match with each other, imaging support device 100 updates parameter 1144 of estimation model 114 such that the types match with each other and the numbers match with each other.

In this way, imaging support device 100 can generate learned model 114a by learning estimation model 114 based on the identification result about the type of the tooth that is obtained using the three-dimensional data obtained by the identification process, assuming that the tooth information (the color information, the tooth name, the tooth number, or the like) corresponding to the type of the tooth associated with the three-dimensional data included in the learning data is defined as correct data.

Further, in the learning process, imaging support device 100 learns estimation model 114 in consideration of the profile data in addition to the learning data, so that it can generate learned model 114a in consideration of the profile of subject 2.

[Learning Process of Server Device]

The learning process performed by server device 500 will be hereinafter described. The learning process is implemented by computing device 530 of server device 500 executing OS 527 and learning program 521.

From the learning data set, server device 500 selects learning data to be used for learning. In this case, the learning data may be generated using the big data accumulated by server device 500 and stored therein. For example, server device 500 may generate, in advance, learning data using three-dimensional data included in the scan information acquired from imaging support device 100 in each of locals A to C and the dental laboratory, and then, perform the learning process using the generated learning data. Server device 500 does not necessarily have to automatically select the learning data, but may use the learning data selected by user 1 for the learning process.

Server device 500 inputs, into estimation model 514, the three-dimensional data (the position information) included in the selected learning data and the profile data of subject 2 as a target to be scanned during generation of the learning data. At this time, the correct data labeled in the three-dimensional data is not input into server device 500. Based on the feature of a tooth corresponding to the three-dimensional data, server device 500 performs the identification process of identifying a type of this tooth by using estimation model 514. In the identification process, based on the profile data in addition to the three-dimensional data, server device 500 identifies a type of the tooth using estimation model 514.

Then, server device 500 updates the parameter of estimation model 514 based on the error between the identification result about the type of the tooth identified by the identification process and the correct data corresponding to the learning data used for learning.

For example, as a result of the identification based on the position information about a specific tooth, server device 500 estimates the color information corresponding to the specific tooth. Server device 500 compares the color information (the correct data) corresponding to the specific tooth included in the learning data set with the color information estimated by server device 500 itself. Then, when these pieces of color information match with each other, server device 500 maintains the parameter of estimation model 514. In contrast, when these pieces of color information do not match with each other, server device 500 updates the parameter of estimation model 514 such that these pieces of color information match with each other.

Alternatively, as a result of the identification based on the position information of a specific tooth, server device 500 estimates the color information corresponding to the specific tooth, and then identifies a type of the tooth and the number of the tooth (correct data) that correspond to the color information based on color classification data 518. Then, server device 500 compares the type of the tooth and the number of the tooth (correct data) that are assigned to the color information corresponding to the specific tooth included in the learning data set with the type of the tooth and the number of the tooth that are estimated by server device 500 itself. When the types match with each other and the numbers match with each other, server device 500 maintains the parameter of estimation model 514. In contrast, when the types do not match with each other and the numbers do not match with each other, server device 500 updates the parameter of estimation model 514 such that the types match with each other and the numbers match with each other.

When learning has been done based on all the pieces of learning data, server device 500 can store learned estimation model 514 as learned model 514a. Then, server device 500 can transmit the generated learned model 514a to imaging support device 100 in each local.

In this way, server device 500 can generate learned model 514a by learning estimation model 514 based on the identification result about the type of the tooth that is obtained using the three-dimensional data obtained by the identification process, assuming that the tooth information (the color information, the tooth name, the tooth number, or the like) corresponding to the type of the tooth associated with the three-dimensional data included in the learning data is defined as correct data.

Further, in the learning process, server device 500 learns estimation model 514 in consideration of the profile data in addition to the learning data, so that it can generate learned model 514a in consideration of the profile of subject 2.

Further, server device 500 uses the three-dimensional data included in the scan information acquired from imaging support device 100 in each of locals A to C and the dental laboratory as the learning data used in the learning process. Thus, server device 500 can perform the learning process based on more learning data than that in the learning process performed for each imaging support device 100, and also, can generate learned model 514a that allows identification of a type of a tooth with higher accuracy.

[Support Process of Imaging Support Device 100]

The following describes the support process performed by imaging support device 100 based on a flowchart. FIG. 9 is a flowchart for illustrating an example of the support process performed by the imaging support device according to the present first embodiment. Each of steps shown in FIG. 9 is implemented by computing device 130 of imaging support device 100 executing OS 127 and specification program 120a.

As shown in FIG. 9, imaging support device 100 determines whether a start condition for a support process I has been satisfied or not (S40). The start condition may be satisfied, for example, when the power supply of three-dimensional scanner 200 is started, or upon switching to a mode corresponding to support process I after the power supply of three-dimensional scanner 200 is started. Alternatively, the start condition may be satisfied when a start switch is operated after an icon corresponding to support process I (for example, an assist icon) is operated and turned into a blinking state. The start condition may be satisfied when a prescribed amount of three-dimensional data is acquired or may be satisfied at a timing at which the entire dental arch is imaged. The start condition may be any condition as long as it is satisfied when any action is performed on three-dimensional scanner 200.

When the start condition has not been satisfied (NO in S40), imaging support device 100 ends the process. On the other hand, when the start condition has been satisfied (YES in S40), imaging support device 100 determines whether the three-dimensional data has been acquired or not (S41). For example, imaging support device 100 determines whether a sufficient amount of three-dimensional data for performing support process I has been input or not. When a sufficient amount of three-dimensional data has not been input (NO in S41), imaging support device 100 repeats the process in S41.

On the other hand, when a sufficient amount of three-dimensional data has been input (YES in S41), imaging support device 100 performs a process of identifying a type of a tooth (S42). Imaging support device 100 identifies a type of a tooth from the input three-dimensional data based on learned model 114a.

Figure 10:
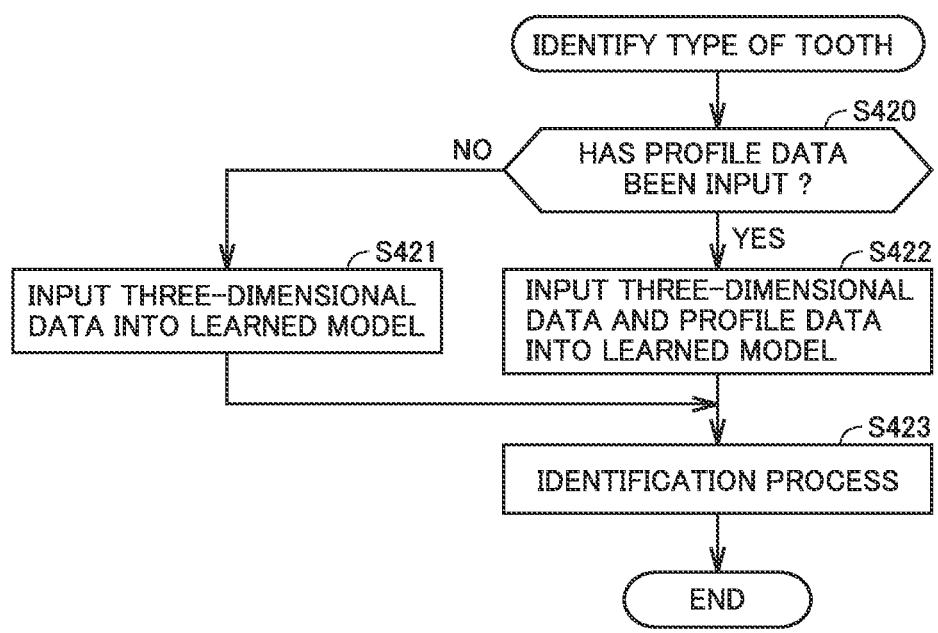
FIG. 10 is a flowchart for illustrating an example of a process of identifying a type of a tooth performed by the imaging support device according to the present first embodiment.

The following further describes a process of identifying a type of a tooth that is performed by imaging support device 100. FIG. 10 is a flowchart for illustrating an example of the process of identifying a type of a tooth that is performed by imaging support device 100 according to the present first embodiment. Each of steps shown in FIG. 10 is implemented by computing device 130 of imaging support device 100 executing OS 127 and identification program 120. First, it is determined whether the profile data of subject 2 has been input or not by user 1 (S420). When the profile data has not been input (NO in S420), the three-dimensional data (the position information) is input into learned model 114a (S421). On the other hand, when the profile data has been input (YES in S420), imaging support device 100 inputs the three-dimensional data (the position information) and the profile data into learned model 114a (S422). The learned model used in this case is not limited to learned model 114a generated by imaging support device 100, but may be learned model 514a generated by server device 500.

After S421 and S422, based on the feature of a tooth corresponding to the three-dimensional data, imaging support device 100 performs an identification process of identifying a type of this tooth using learned model 114a (S423). In this case, when the profile data has been input into learned model 114a in S422, imaging support device 100 identifies a type of the tooth using learned model 114a based on the profile data in addition to the three-dimensional data. In this case, the type of the tooth can be identified more accurately than in the case where the type of the tooth is identified using learned model 114a based only on the three-dimensional data.

Referring back to FIG. 9, after performing the process of identifying a type of a tooth in S42, imaging support device 100 determines whether there is insufficient three-dimensional data or not in the acquired three-dimensional data (S43). For example, imaging support device 100 determines whether or not there is a portion where the acquired three-dimensional data does not exceed a predetermined amount of data. When there is insufficient three-dimensional data (YES in S43), based on the type of the tooth identified in S42, imaging support device 100 specifies a type of a tooth in the portion where three-dimensional data is insufficient, and outputs the specification result to display 300, speaker 400, and the like (S44), and then, ends the present process. When there is not insufficient three-dimensional data (NO in S43), imaging support device 100 ends the present process.

In this way, imaging support device 100 specifies the type of the tooth for which the amount of data is insufficient in the acquired three-dimensional data, and thereby can inform user 1 about the type of the tooth to be re-scanned (re-measured). Based on the feature of the tooth corresponding to the input three-dimensional data, imaging support device 100 identifies a type of this tooth using learned model 114a. Thereby, imaging support device 100 can identify a type of a tooth more accurately than in the case where a type of a tooth is identified depending on the user's knowledge, and thus, can accurately specify the type of the tooth to be re-scanned and inform user 1 about the specified type of the tooth.

Further, in the identification process, imaging support device 100 identifies a type of a tooth in consideration of the profile data in addition to the input three-dimensional data, thereby allowing more accurate identification of a type of a tooth.

The above description is predicated on that, at the timing at which the entire dental arch is imaged, imaging support device 100 specifies the type of the tooth in a sufficient portion not exceeding a predetermined amount of data (not satisfying a prescribed criterion) in the acquired three-dimensional data, and then, outputs the specification result to display 300. However, without being limited to the above, at the timing of imaging a prescribed range in which an image of about ½, about ⅓, about ⅔, about ⅕, about ⅖, about ⅗, or about ⅘ of the dental arch can be formed, imaging support device 100 may specify the type of the tooth in the sufficient portion and then output the specification result to display 300. Of course, imaging support device 100 may output the information (for example, an insufficient portion) about the type of the tooth specified by specification unit 1150 to the outside at the timing at which a prescribed number of teeth are imaged or at the timing of prescribed time intervals.

Figure 11:
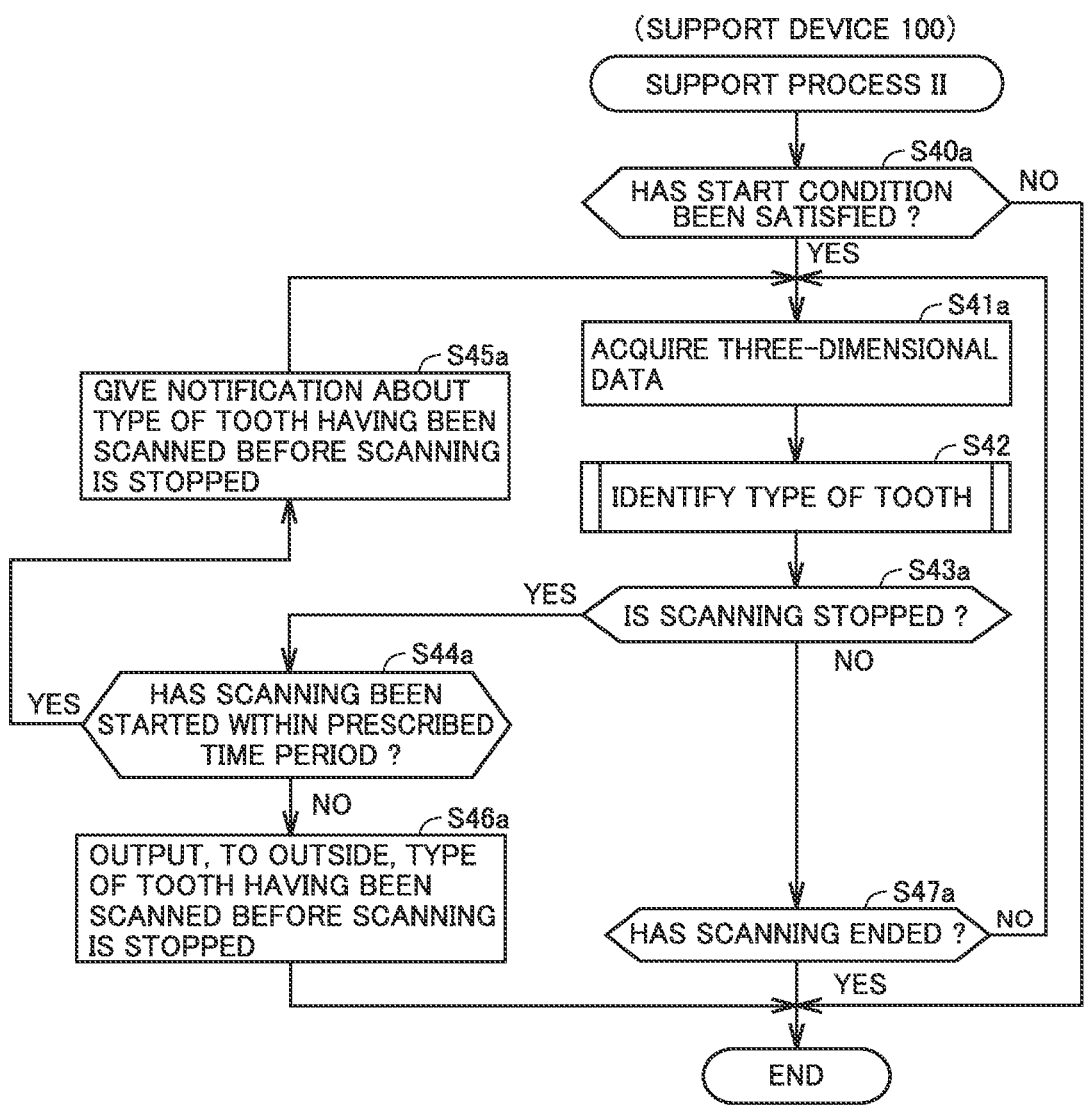
FIG. 11 is a flowchart for illustrating another example of the support process performed by the imaging support device according to the present first embodiment.

Support process I has been described as a process of specifying the type of the tooth in an insufficient portion in which the information obtained from the three-dimensional data does not exceed a predetermined amount of data, and then, outputting the specification result as support information. However, without being limited to the above, imaging support device 100 can perform another support process of specifying the type of the tooth and providing user 1 with the specification result as support information. For example, as another example, the following describes a support process II of specifying the type of the tooth imaged before imaging is stopped, and providing user 1 with the specified information as support information when imaging is started within a prescribed time period. FIG. 11 is a flowchart for illustrating another example of the support process performed by the imaging support device according to the present first embodiment. Each of steps shown in FIG. 11 is implemented by computing device 130 of imaging support device 100 executing OS 127 and specification program 120a.

As shown in FIG. 11, imaging support device 100 determines whether a start condition for a support process II has been satisfied or not (S40a). The start condition may be satisfied, for example, when the power supply of three-dimensional scanner 200 is started, or upon switching to a mode corresponding to support process II after the power supply of three-dimensional scanner 200 is started. Alternatively, the start condition may be satisfied when a start switch is operated after an icon corresponding to support process II (for example, an assist icon) is operated and turned into a blinking state. The start condition may be any condition as long as it is satisfied when any action is performed on three-dimensional scanner 200.

When the start condition has not been satisfied (NO in S40a), imaging support device 100 ends the process. On the other hand, when the start condition has been satisfied (YES in S40a), imaging support device 100 acquires three-dimensional data (S41a). When a sufficient amount of three-dimensional data has been input, imaging support device 100 performs a process of identifying a type of a tooth (S42). In the process shown in FIG. 10, imaging support device 100 identifies a type of a tooth from the input three-dimensional data based on learned model 114a.

Imaging support device 100 determines whether scanning of teeth by three-dimensional scanner 200 is stopped or not (S43a). In this case, the timing at which it is determined that scanning is stopped may be the timing at which imaging support device 100 receives an imaging stop signal, or may be the timing at which input unit 1102 does not receive a tooth image for a prescribed time period or more.

When it is determined that scanning is stopped (YES in S43a), imaging support device 100 determines whether or not scanning of teeth by three-dimensional scanner 200 has been started within a prescribed time period (for example, within 3 minutes after scanning is stopped) (S44a). When scanning has been started within the prescribed time period (YES in S44a), then, based on the type of the tooth identified in S42, imaging support device 100 specifies the type of the tooth scanned before scanning is stopped, and then, notifies user 1 about the specification result (S45a). For example, imaging support device 100 outputs the specification result to display 300, speaker 400, and the like to thereby notify user 1 about the specification result. Accordingly, user 1 can start scanning of teeth by three-dimensional scanner 200 from an appropriate position based on the type of the tooth that has been scanned before scanning is stopped. The specification result of which user 1 is notified may include information about, the type of one tooth scanned before scanning is stopped, information about the type of the tooth adjacent to this one tooth, and both pieces of information.

Imaging support device 100 gives a notification about the type of the tooth scanned before scanning is stopped, and then returns the process to S41*a*. When scanning is not started within a prescribed time period (NO in S44*a*), imaging support device 100 outputs, to the outside, the type of the tooth having been scanned before scanning is stopped (S46*a*), and then, ends the present process.

When it is determined that scanning is not stopped (NO in S43*a*), imaging support device 100 determines whether scanning of teeth by three-dimensional scanner 200 has ended or not (S47*a*). When scanning of teeth has not ended (NO in S47*a*), imaging support device 100 returns the process to S41*a*. When scanning of teeth ended (YES in S47*a*), imaging support device 100 ends the present process.

Figure 12:
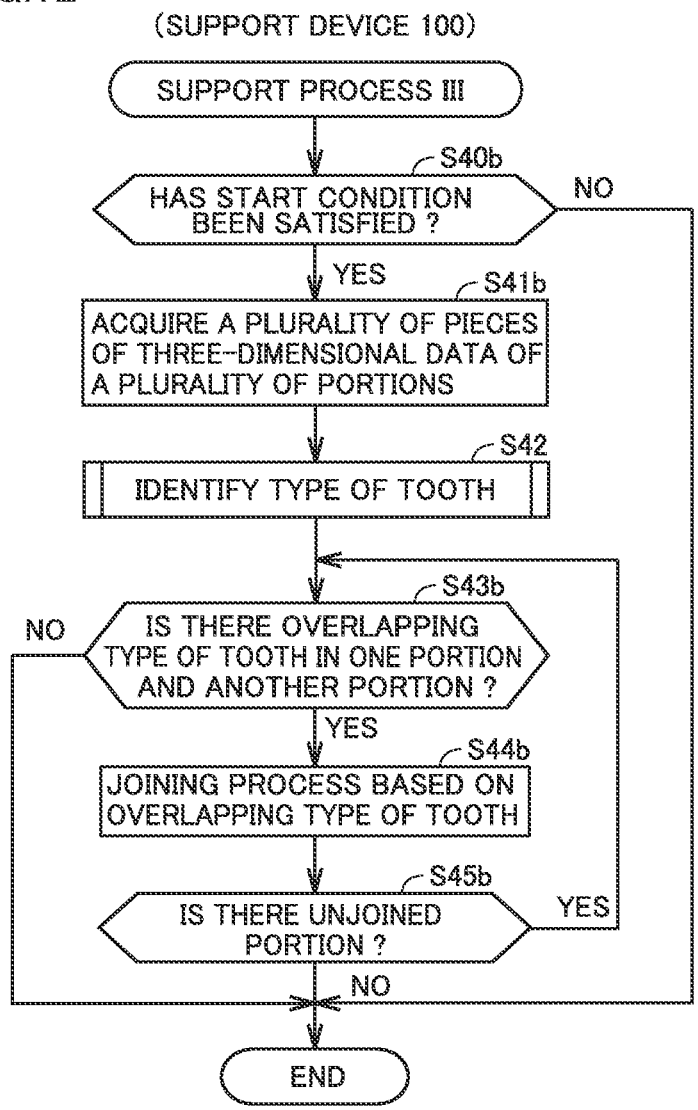
FIG. 12 is a flowchart for illustrating still another example of the support process performed by the imaging support device according to the present first embodiment.

As still another example, the following describes a support process III in which, when a plurality of three-dimensional images (three-dimensional data) are joined together, a type of a tooth is specified and provided to user 1 as support information. FIG. 12 is a flowchart for illustrating still another example of the support process performed by the imaging support device according to the present first embodiment. Each of steps shown in FIG. 12 is implemented by computing device 130 of imaging support device 100 executing OS 127 and specification program 120*a*.

As shown in FIG. 12, imaging support device 100 determines whether a start condition for a support process III has been satisfied or not (S40*b*). The start condition may be satisfied, for example, when the power supply of three-dimensional scanner 200 is started, or upon switching to a mode corresponding to support process III after the power supply of three-dimensional scanner 200 is started. Alternatively, the start condition may be satisfied when a start switch is operated after an icon corresponding to support process III (for example, an assist icon) is operated and turned into a blinking state. The start condition may be any condition as long as it is satisfied when any action is performed on three-dimensional scanner 200.

When the start condition has not been satisfied (NO in S40*b*), imaging support device 100 ends the present process. On the other hand, when the start condition has been satisfied (YES in S40*b*), imaging support device 100 acquires a plurality of pieces of three-dimensional data of a plurality of portions (S41*b*). For example, when scanning a dental arch, imaging support device 100 divides the dental arch into thirds, and scans the divided three portions to acquire three pieces of three-dimensional data. When the plurality of pieces of three-dimensional data of the plurality of portions are input, imaging support device 100 performs a process of identifying a type of a tooth for each three-dimensional data (S42). In the process shown in FIG. 10, imaging support device 100 identifies the type of the tooth from the plurality of pieces of input three-dimensional data of the respective portions based on learned model 114*a*.

Imaging support device 100 determines whether there is an overlapping type of a tooth in one portion and another portion in the plurality of pieces of three-dimensional data of the respective portions (S43*b*). When there is an overlapping type of a tooth in one portion and another portion (YES in S43*b*), imaging support device 100 performs a process of joining the three-dimensional data of one portion and the three-dimensional data of another portion based on the overlapping type of the tooth (S44*b*). For example, when imaging support device 100 acquires three-dimensional data of: a portion (one portion) obtained by scanning an area from the third molar to the first premolar on the right side in the upper jaw; and a portion (another portion) obtained by scanning an area from the first premolar to the central incisor on the right side in the upper jaw, imaging support device 100 determines that the first premolar of one portion overlaps the first premolar of another portion. Since there is an overlapping type of a tooth, imaging support device 100 joins the three-dimensional data of one portion and the three-dimensional data of another portion with respect to the first premolar to thereby form one piece of three-dimensional data.

Imaging support device 100 determines whether or not there is an unjoined portion in the plurality of pieces of three-dimensional data of the respective portions (S45*b*). When there is an unjoined portion (YES in S45*b*), imaging support device 100 returns the process to S43*b*. When there is not an unjoined portion (NO in S45*b*) or there is not an overlapping type of a tooth in one portion and another portion (NO in S43*b*), imaging support device 100 ends the present process.

Even when imaging support device 100 scans the dental arch separately several times and acquires a plurality of pieces of three-dimensional data of a plurality of portions, imaging support device 100 can still easily join the plurality of pieces of three-dimensional data into one piece of three-dimensional data by performing the above-mentioned support process III. If user 1 joins a plurality of pieces of three-dimensional data of a plurality of portions without performing the above-mentioned support process III, user 1 needs to perform an operation to visually determine the type of the tooth from each of the pieces of three-dimensional data and join these pieces of three-dimensional data together, with the result that the operation becomes complicated.

The above-mentioned support processes I to III can be separately performed in imaging support device 100, but may be performed in various combinations. For example, imaging support device 100 may perform support processes I and II in combination to conduct scanning to thereby specify a type of a tooth for which the amount of data is insufficient. Also, when scanning is stopped, imaging support device 100 may specify a type of a tooth before stopping of scanning. In this case, for example, when scanning is started within a prescribed time period after scanning is stopped, imaging support device 100 gives a notification preferentially about the type of the tooth for which the amount of data is insufficient. Then, when re-scanning is performed for the type of the tooth for which the amount of data is insufficient, imaging support device 100 gives a notification about the type of the tooth that has been scanned before scanning is stopped. Of course, imaging support device 100 may reverse the order of notification.

As described above, imaging support device 100 according to the present first embodiment is an imaging support device that supports imaging of teeth inside an oral cavity. Imaging support device 100 includes an input unit 1102, an identification unit 1130, a specification unit 1150, and an output unit 1103. Input unit 1102 receives a tooth image obtained by imaging the teeth inside the oral cavity. Identification unit 1130 identifies a type of a tooth based on the tooth image received by input unit 1102. Based on the type of the tooth identified by identification unit 1130, specification unit 1150 specifies a type of a tooth as a target for imaging support. Output unit 1103 outputs information about the type of the tooth specified by specification unit 1150 to an outside at a prescribed timing.

Accordingly, imaging support device 100 specifies a type of a tooth as a target for imaging support based on the type of the tooth identified by identification unit 1130, and thereby can output the information for imaging support to a user 1 so as to allow user 1 to easily recognize which tooth inside the oral cavity corresponds to the tooth as a target for imaging support.

Specification unit 1150 specifies a type of a tooth that needs to be imaged for user 1, and output unit 1103 outputs information about the type of the tooth specified by specification unit 1150 to the outside before user 1 performs imaging.

Accordingly, imaging support device 100 allows user 1 to easily recognize a tooth to be imaged next.

As a type of a tooth that needs to be imaged for user 1, specification unit 1150 specifies a type of a tooth for which information obtained from the tooth image fails to satisfy a prescribed criterion. For example, when three-dimensional scanner 200 scans teeth, the type of the tooth in a portion not exceeding a predetermined amount of data in the three-dimensional data obtained from the tooth image is specified based on the type of the tooth identified by identification unit 1130.

Accordingly, imaging support device 100 allows user 1 to recognize the type of the tooth for which the amount of data is insufficient, and thereby can urge user 1 to perform imaging again.

As a type of a tooth that needs to be imaged for user 1, specification unit 1150 specifies a type of a tooth that is imaged at a timing at which imaging is stopped, and output unit 1130 outputs, to the outside, at least one piece of information of: the type of the tooth specified by specification unit 1150 before a timing at which user 1 starts imaging; and a type of a tooth adjacent to the specified type of the tooth.

Accordingly, when imaging support device 100 starts imaging within a prescribed time period after imaging is stopped, imaging support device 100 allows user 1 to recognize the type of the first tooth from which imaging is started, thereby allowing efficient imaging to be performed.

When a new tooth image is not input into input unit 1102 for a prescribed time pend from the timing at which imaging is stopped to the timing at which imaging is started, output unit 1103 may output information about the specified type of the tooth to the outside.

Accordingly, when imaging is not started within a prescribed time period after it is determined that imaging is stopped, user 1 is highly likely to perform an imaging operation again or shift to imaging of another patient. Thus, imaging support device 100 outputs, to the outside, the information about the type of the tooth specified at the timing at which imaging is stopped, and thereby can prevent the function of support process II from being performed.

Output unit 1103 outputs information about the type of the tooth specified by specification unit 1150 to the outside at a timing at which the dental arch in a prescribed range is imaged. The prescribed range is a range in which an image of about ½, about ⅓, about ⅔, about ⅕, about ⅖, about ⅗, or about ⅘ of the dental arch can be formed. Further, output unit 1103 outputs information about the type of the tooth specified by the specification unit to the outside at a timing at which a prescribed number of teeth are imaged.

Accordingly, imaging support device 100 notifies user 1 about the specified type of the tooth (for example, the type of the tooth for which the amount of data is insufficient) at the timing at which a prescribed range of the dental arch is imaged or at the timing at which a prescribed number of teeth are imaged, thereby reducing complicatedness.

Input unit 1102 receives three-dimensional data corresponding to a three-dimensional image of the dental arch from three-dimensional scanner 200, and specification unit 1150 specifies a type of a tooth for which information is insufficient in the three-dimensional data input from input unit 1102.

Accordingly, imaging support device 100 allows user 1 to easily recognize the type of the tooth for which the amount of data is insufficient, and thereby can provide user 1 accurately with the information about the type of the tooth to be measured again.

Specification unit 1150 specifies an overlapping type of a tooth among the tooth images as a type of a tooth used for joining.

This allows imaging support device 100 to easily join a plurality of tooth images together.

Based on a feature of a tooth corresponding to the tooth image input from input unit 1102, identification unit 1130 identifies a type of the tooth using an estimation model 114 including a neural network. Estimation model 114 is learned based on: tooth information corresponding to a type of a tooth associated with the tooth image; and an identification result of the type of the tooth that is obtained using the tooth image.

Accordingly, user 1 inputs three-dimensional data including data of the tooth into estimation model 114 (learned model 114a) including neural network 1142, and thus, can identify a type of the tooth, thereby allowing more accurate identification of a type of a tooth than in the case where a type of a tooth is identified depending on the user's knowledge.

Input unit 1102 receives a tooth image including a plurality of teeth, and identification unit 1130 identifies a type of each of the teeth based on a feature of each of the teeth corresponding to the tooth image.

Accordingly, user 1 inputs a tooth image including a plurality of teeth into estimation model 114 (learned model 114a) including neural network 1142, and thereby, can identify a type of each of the teeth. Thus, a type of a tooth can be identified more accurately and smoothly than in the case where types of teeth are identified one by one depending on the user's knowledge. Further, user 1 can extract a feature of a tooth by estimation model 114 including neural network 1142 also in consideration of the relation with the shapes of the adjacent teeth, thereby allowing accurate identification of a type of a tooth.

The tooth image includes three-dimensional position information at each of points of a tooth.

Accordingly, user 1 inputs the three-dimensional position information at each of a plurality of points forming a tooth corresponding to the three-dimensional data into estimation model 114 (learned model 114a) including neural network 1142, and thereby, can identify a type of the tooth.

Estimation model 114 is learned based on attribute information related to a subject having teeth, in addition to the tooth information and the identification result obtained by identification unit 1130.

Accordingly, user 1 can implement learning of estimation model 114 based on the attribute information related to subject 2 in addition to the learning data, thereby allowing generation of a learned model in consideration of the attribute information about subject 2.

The attribute information includes at least one piece of information of an age, a gender, a race, a height, a weight, and a place of residence about the subject.

Accordingly, user 1 can implement learning of estimation model 114 based on at least one of an age, a gender, a race, a height, a weight, and a place of residence about the subject in addition to the learning data, thereby allowing generation of learned model 114a in consideration of the profile of subject 2.

A scanner system 10 that acquires shape information of a tooth includes: a three-dimensional scanner 200 that images teeth using a three-dimensional camera; and an imaging support device 100 that identifies a type of a tooth based on a tooth image in three dimensions that is acquired by three-dimensional scanner 200 and gives a notification about the identified type of the tooth. Imaging support device 100 includes: an input unit 1102 that receives a tooth image obtained by imaging teeth inside an oral cavity; an identification unit 1130 that identifies a type of a tooth based on the tooth image received by input unit 1102; a specification unit 1150 that, based on the type of the tooth identified by identification unit 1130, specifies a type of a tooth as a target to be imaged; and an output unit 1103 that outputs information about the type of the tooth specified by specification unit 1150 to an outside at a prescribed timing.

Accordingly, scanner system 10 specifies a type of a tooth as a target for imaging support based on the type of the tooth identified by identification unit 1130, and thereby can output the information for imaging support to user 1 so as to allow user 1 to easily recognize which tooth inside the oral cavity corresponds to the tooth as a target for imaging support.

An imaging support method of supporting imaging of teeth inside an oral cavity includes: receiving a tooth image obtained by imaging the teeth inside the oral cavity; identifying a type of a tooth based on the received tooth image; based on the identified type of the tooth, specifying a type of a tooth as a target to be imaged; and outputting information about the specified type of the tooth to an outside at a prescribed timing.

Thus, according to the imaging support method, a type of a tooth is specified as a target for imaging support based on the identified type of the tooth, and thereby, the information for imaging support can be output to user 1 so as to allow user 1 to easily recognize which tooth inside the oral cavity corresponds to the tooth as a target for imaging support.

Second Embodiment

In the above description, imaging support device 100 according to the first embodiment is configured to perform a process of automatically identifying a type of a tooth with the help of AI based on three-dimensional data acquired by three-dimensional scanner 200 to specify a type of a tooth as a target for imaging support. However, without being limited to the above, imaging support device 100 may be configured to perform a process of automatically identifying a type of a tooth with no help of AI based on the three-dimensional data acquired by three-dimensional scanner 200 and specifying a type of a tooth as a target for imaging support. For example, it is conceivable to perform a process of automatically identifying a type of a tooth by pattern matching of the three-dimensional image acquired by three-dimensional scanner 200 and specifying a type of a tooth as a target for imaging support.

Figure 13:
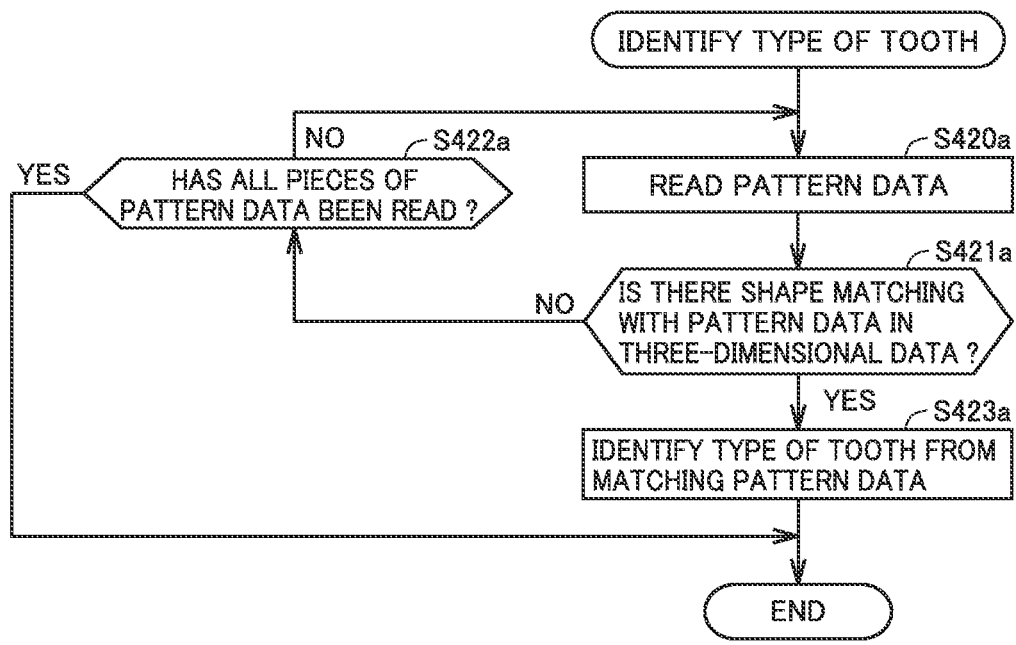
FIG. 13 is a flowchart for illustrating an example of a process of identifying a type of a tooth performed by an imaging support device according to the present second embodiment.

The following describes a process of identifying a type of a tooth performed by an imaging support device according to the present second embodiment. FIG. 13 is a flowchart for illustrating an example of a process of identifying a type of a tooth performed by the imaging support device according to the present second embodiment. The imaging support device according to the present second embodiment has the same configuration as that of imaging support device 100 described with reference to FIGS. 3 and 5 except that estimation model 114 is not used, and thus, the detailed description thereof will not be repeated. Each of steps shown in FIG. 13 is implemented by computing device 130 of the imaging support device executing OS 127 and identification program 120.

First, the imaging support device reads pattern data stored in advance in a storage or the like (S420a). For example, an image of a tooth to be identified as shown in FIG. 8 is stored in the storage, and the imaging support device reads an image used as pattern data for pattern matching from the storage.

The imaging support device compares the three-dimensional image acquired by three-dimensional scanner 200 with the pattern data read from the storage, to determine whether or not there is a matching shape (S421a). For example, the imaging support device calculates a normalized correlation between the three-dimensional image acquired by three-dimensional scanner 200 and the pattern data read from the storage to thereby determine whether the shapes match with each other.

When there is no matching shape (NO in S421a), the imaging support device determines whether all the pieces of pattern data stored in advance in the storage or the like have been read or not (S422a). When all the pieces of pattern data have not been read (NO in S422a), the imaging support device returns the process to S420a and reads another pattern data (S420a).

When there is a matching shape (YES in S421a), the imaging support device identifies a type of a tooth of the three-dimensional image acquired from the pattern data including a matching shape (S423a). For example, when the three-dimensional image acquired by three-dimensional scanner 200 matches in shape with the pattern data of the third molar on the right side in the upper jaw, the imaging support device identifies the type of the tooth in the acquired three-dimensional image as the third molar on the right side in the upper jaw.

When all the pieces of pattern data have been read (YES in S422a), and the type of the tooth is identified from the pattern data including a matching shape (S423a), then, the imaging support device ends the present process. The process of identifying a type of a tooth shown in FIG. 13 can be applicable to the process of identifying a type of a tooth (S42) included in support process I shown in FIG. 9, support process II shown in FIG. 11, and support process III shown in FIG. 12.

As described above, the imaging support device according to the present second embodiment is an imaging support device that supports imaging of teeth inside an oral cavity. The imaging support device includes an input unit, an identification unit, a specification unit, and an output unit. The input unit receives a tooth image obtained by imaging the teeth inside the oral cavity. The identification unit identifies a type of a tooth by pattern matching with no help of AI, for example, based on the tooth image received by the input unit. The specification unit specifies a type of a tooth as a target for imaging support based on the type of the tooth identified by the identification unit. The output unit outputs information about the type of the tooth specified by the specification unit to an outside at a prescribed timing.

Accordingly, the imaging support device specifies a type of a tooth as a target for imaging support based on the type of the tooth identified by the identification unit, and thereby can output the information for imaging support to user 1 so as to allow user 1 to easily recognize which tooth inside the oral cavity corresponds to the tooth as a target for imaging support.

(Modifications)

(a) In the description in the first and second embodiments, the imaging support device supports a three-dimensional scanner (an intraoral scanner) for acquiring a three-dimensional shape of a tooth inside the oral cavity. However, the imaging device supported by the imaging support device is not limited to a three-dimensional scanner for an oral cavity, but can be applicable to an imaging device having a similar configuration, for example, can be applicable also to a three-dimensional scanner capable of imaging the inside of a human ear other than the inside of the oral cavity to acquire a three-dimensional shape inside the outer ear, and also, can be applicable to a desktop scanner capable of acquiring a three-dimensional shape of a jaw and dentition model.

It should be noted that the three-dimensional scanners according to the present first and second embodiments each may be configured to acquire a three-dimensional shape using a technique such as a confocal method, a triangulation method, a white light interferometry method, a stereo method, a photogrammetry method, a simultaneous localization and mapping (SLAM) method, an optical coherence tomography (OCT) method, and the like, in addition to the configuration of acquiring a three-dimensional shape using a technique of a focus method.

(b) In the first and second embodiments, the imaging device supported by the imaging support device includes, for example, an intraoral camera, an optical coherence tomography (OCT), an ultraviolet/infrared/terahertz imaging device, a fluorescent imaging device, and the like.

(c) The first and second embodiments have been described with regard to a scanner system including an imaging support device and a three-dimensional scanner connected to each other. However, the imaging support device is not limited to the above, but may have a configuration in which an imaging support device is mounted on a three-dimensional scanner, or a configuration in which an imaging support device is connected to a three-dimensional scanner through a network. Further, the imaging support device may be provided in the form of a cloud service in which a plurality of three-dimensional scanners are connected through a network.

(d) In the description in the present first and second embodiments, the imaging support device specifies a type of a tooth for which the amount of data is insufficient in the acquired three-dimensional data, and informs a user about the type of the tooth to be re-scanned (re-measured) as support information. Further, for example, when the user erroneously scans the buccal side in place of the tongue side during re-scanning after a notification given to the user about the type of the tooth for which the amount of data is insufficient, the imaging support device may further specify the erroneous scanning and give a notification again. Specifically, based on the value from a motion sensor provided in the three-dimensional scanner, the imaging support device determines whether or not the three-dimensional scanner is disposed at the inclination different from the intended inclination defined in the content included in the notification. In the case of an error, the imaging support device gives a notification again.

(e) In the description in the present first and second embodiments, the imaging support device specifies a type of a tooth for which the amount of data is insufficient in the acquired three-dimensional data, to thereby inform the user about the type of the tooth to be re-scanned (re-measured) as support information. The number of teeth for which the amount of data is insufficient is not limited to one, but may be more than one. When there are a plurality of teeth for which the amount of data is insufficient, the imaging support device gives a notification about the types of teeth, for example, in descending order of the degree of insufficiency of the amount of data. In this way, by giving a notification in descending order of the degree of insufficiency of the amount of data, entirely highly valuable three-dimensional data can be achieved.

(f) In the description in the present first and second embodiments, the imaging support device specifies a type of a tooth for which the amount of data is insufficient in the acquired three-dimensional data, and then notifies the user about the specified type of the tooth. However, without being limited thereto, it is conceivable that the imaging support device may notify the user about overlapping data when the user uses the three-dimensional scanner to try to scan a tooth for which data overlaps in the acquired three-dimensional data. For example, when the user wastefully scans a, canine with the three-dimensional scanner even though the three-dimensional data of this canine is sufficiently acquired, the imaging support device gives a notification such as "scanning of canine is not required (is sufficient)". Thus, the imaging support device can prevent unnecessary data from being stored in the memory of the three-dimensional scanner, and thereby, the storage capacity can be ensured and calculation delay can be avoided.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims.

REFERENCE SIGNS LIST 1 user, 2 subject, 5 network, 10 scanner system, 100 imaging support device, 102 scanner interface 103, 503 display interface, 104 speaker interface, 105, 505 peripheral interface, 106, 506 network controller, 107, 507 medium reading device, 108 PC display, 109, 509 memory, 110, 510 storage, 112, 512 scan information, 114, 514 estimation model, 114a, 514a learned model, 116, 516 learning data set, 118, 518 color classification data, 119, 519 profile data, 120 identification program, 120a specification program, 121, 521 learning program, 122, 522 three-dimensional data, 124, 524 identification result, 127, 527 OS, 130, 530 computing device, 200 three-dimensional scanner, 300, 350 display, 400 speaker, 500 server device, 550 removable disk 601, 651 keyboard, 602, 652 mouse, 1102 input unit, 1103 output unit, 1119 profile acquisition unit, 1130 identification unit, 1142 neural network, 1144 parameter, 1150 specification unit.

The invention claimed is:

1. An imaging support device that supports imaging of teeth inside an oral cavity, the imaging support device comprising:
   an input unit that receives three-dimensional data including data of the teeth obtained by imaging the teeth inside the oral cavity;
   an identification unit that identifies a type of a tooth based on the three-dimensional data;
   a specification unit that, based on the type of the tooth identified by the identification unit, specifies a type of a tooth corresponding to a portion of the three-dimensional data that does not exceed a predetermined amount of data as a target for imaging support and predicts a type of a tooth to be imaged next; and an output unit that outputs, as imaging support, information about the type of the tooth specified by specification unit and the type of the tooth to be imaged next.

2. The imaging support device according to claim 1, wherein
the specification unit specifies a type of a tooth that needs to be imaged for a user, and
the output unit outputs information about the type of the tooth specified by the specification unit before the user performs imaging.

3. The imaging support device according to claim 2, wherein, as a type of a tooth that needs to be imaged for the user, the specification unit specifies a type of a tooth for which information obtained from the tooth image fails to satisfy a prescribed criterion.

4. The imaging support device according to claim 1, wherein
as a type of a tooth that needs to be imaged for a user, the specification unit specifies a type of a tooth that is imaged at a timing at which imaging is stopped, and
the output unit outputs at least one piece of information of:
the type of the tooth specified by the specification unit before a timing at which the user starts imaging; and
a type of a tooth adjacent to the specified type of the tooth.

5. The imaging support device according to claim 4, wherein the timing at which imaging is stopped is a timing at which the imaging support device receives an imaging stop signal.

6. The imaging support device according to claim 4, wherein, when a new tooth image is not input to the input unit during a prescribed time period from the timing at which imaging is stopped to the timing at which imaging is started, the output unit outputs information about the specified type of the tooth.

7. The imaging support device according to claim 1, wherein the imaging support device supports a scanning device that forms an image of a dental arch by joining a plurality of tooth images obtained by scanning and imaging an inside of the oral cavity.

8. The imaging support device according to claim 7, wherein the output unit outputs information about the type of the tooth specified by the specification unit at a timing at which a prescribed number of teeth are imaged.

9. The imaging support device according to claim 7, wherein
the input unit receives three-dimensional data corresponding to a three-dimensional image of the dental arch from the scanning device, and
the specification unit specifies a type of a tooth for which information is insufficient in the three-dimensional data input from the input unit.

10. The imaging support device according to claim 7, wherein the specification unit specifies an overlapping type of a tooth among the tooth images as a type of a tooth used for joining.

11. The imaging support device according to claim 1, wherein
based on a feature of a tooth corresponding to the tooth image input from the input unit, the identification unit identifies a type of the tooth using an estimation model including a neural network, and the estimation model is learned based on:
tooth information corresponding to a type of a tooth associated with the tooth image; and
an identification result of the type of the tooth that is obtained using the tooth image.

12. The imaging support device according to claim 11, wherein
the input unit receives a tooth image including a plurality of teeth, and
the identification unit identifies a type of each of the teeth based on a feature of each of the teeth corresponding to the tooth image.

13. The imaging support device according to claim 11, wherein the tooth image includes three-dimensional position information at each of points of a tooth.

14. The imaging support device according to claim 11, wherein the estimation model is learned based on attribute information related to a subject having teeth in addition to the tooth information and the identification result obtained by the identification unit.

15. The imaging support device according to claim 14, wherein the attribute information includes at least one piece of information of an age, a gender, a race, a height, a weight, and a place of residence about the subject.

16. A scanner system for imaging teeth inside an oral cavity, the scanner system comprising:
a three-dimensional scanner that images the teeth using a three-dimensional camera and acquires three-dimensional data including data of the teeth; and
an imaging support device that
identifies a type of a tooth based on the three-dimensional data, and
gives a notification about the identified type of the tooth, wherein
the imaging support device includes
an input unit that receives the three-dimensional data,
an identification unit that identifies a type of a tooth based on the three-dimensional data,
a specification unit that, based on the type of the tooth identified by the identification unit, specifies a type of a tooth corresponding to a portion of the three-dimensional data that does not exceed a predetermined amount of data as a target for imaging support and predicts a type of a tooth to be imaged next, and
an output unit that outputs, as imaging support, information about the type of the tooth specified by specification unit and the type of the tooth to be imaged next.

17. An imaging support method of supporting imaging of teeth inside an oral cavity, the method comprising:
receiving three-dimensional data including data of the teeth obtained by imaging the teeth inside the oral cavity;
identifying a type of a tooth based on the three-dimensional data;
based on the identified type of the tooth, specifying a type of a tooth corresponding to a portion of the three-dimensional data that does not exceed a predetermined amount of data as a target for imaging support and predicting a type of a tooth to be imaged next; and
outputting, as imaging support, information about the type of the tooth specified by specification unit and the type of the tooth to be imaged next.

* * * * *